United States Patent
Gerstenhaber et al.

(10) Patent No.: US 10,005,219 B2
(45) Date of Patent: Jun. 26, 2018

(54) ROBOTIC ELECTROPROSESSING SYSTEM AND METHOD

(71) Applicant: Temple University—Of The Commonwealth System of Higher Education, Philadelphia, PA (US)

(72) Inventors: Jonathan A. Gerstenhaber, Philadelphia, PA (US); Peter I. Lelkes, Cherry Hill, NJ (US); Yah-el Har-el, Philadelphia, PA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 0 days. days.

(21) Appl. No.: 14/913,915

(22) PCT Filed: Aug. 22, 2014

(86) PCT No.: PCT/US2014/052297
§ 371 (c)(1),
(2) Date: Feb. 23, 2016

(87) PCT Pub. No.: WO2015/027156
PCT Pub. Date: Feb. 26, 2015

(65) Prior Publication Data
US 2016/0214303 A1    Jul. 28, 2016

Related U.S. Application Data

(60) Provisional application No. 61/869,326, filed on Aug. 23, 2013.

(51) Int. Cl.
*D01D 5/00* (2006.01)
*B29C 47/00* (2006.01)
(Continued)

(52) U.S. Cl.
CPC ........ *B29C 47/0076* (2013.01); *A61F 2/3094* (2013.01); *A61F 2/32* (2013.01);
(Continued)

(58) Field of Classification Search
CPC .................................................. D01D 5/0061
See application file for complete search history.

(56) References Cited

U.S. PATENT DOCUMENTS

2008/0141936 A1    6/2008  Pui et al.
2009/0028921 A1*   1/2009  Arinzeh .................... A61F 2/28
                                                    424/423
(Continued)

OTHER PUBLICATIONS

Deitzel, J.M. et al., "Controlled deposition of electrospun poly(ehtylene oxide) fibers", 2001, Polymer, 42: 8163-8170.
(Continued)

*Primary Examiner* — Cachet I Sellman
(74) *Attorney, Agent, or Firm* — Riverside Law, LLP

(57) ABSTRACT

The present invention includes a robotic system for the enhanced automation, manipulation, and control of electroprocessing in two or three dimensions. In one embodiment, the system includes a sealed chamber devoid of any electrical or conductive components which would interfere with the electrical field and eventual material fabrication, while still allowing for two-dimensional and three-dimensional robot motion. In certain embodiments, the system of the invention produces materials or scaffolds with complex shapes, including materials with ridges, valleys, curves, and the like, which are difficult or impossible to construct using traditional systems.

27 Claims, 20 Drawing Sheets

(51) Int. Cl.
| | | |
|---|---|---|
| A61F 2/30 | (2006.01) | |
| A61F 2/32 | (2006.01) | |
| B05D 1/04 | (2006.01) | |
| B29C 47/02 | (2006.01) | |
| B29K 25/00 | (2006.01) | |
| B29L 31/00 | (2006.01) | |

(52) U.S. Cl.
CPC .......... B05D 1/045 (2013.01); B29C 47/0014 (2013.01); B29C 47/025 (2013.01); D01D 5/0061 (2013.01); *A61F 2002/30978* (2013.01); *A61F 2002/30983* (2013.01); *A61F 2002/30985* (2013.01); *A61F 2240/001* (2013.01); *B29K 2025/06* (2013.01); *B29K 2995/0056* (2013.01); *B29L 2031/7532* (2013.01)

(56) References Cited

U.S. PATENT DOCUMENTS

| | | | | |
|---|---|---|---|---|
| 2010/0222771 | A1* | 9/2010 | Mitchell | A61L 27/14 606/1 |
| 2012/0171383 | A1* | 7/2012 | Christensen | B05B 13/0426 427/427.3 |
| 2013/0189435 | A1* | 7/2013 | Mackie | B29C 67/0055 427/256 |
| 2014/0141152 | A1* | 5/2014 | Sostek | A61F 2/04 427/2.24 |

OTHER PUBLICATIONS

Leach, Michelle K. et al., "Electrospinning Fundamentals: Optimizing Solution and Apparatus Parameters", 2011, J Vis Exp, 47: e2494.

Li, Mengyan et al., "Electrospun protein fibers as matrices for tissue engineering", 2005, Biomaterials, 26: 5999-6008.

Lelkes et al., 2008, 10 Electrospinning of natural proteins for tissue engineering scaffolding in: Handbook of Natural-based Polymers for Biomedical Applications (Rui L.Reis editor), pp. 446-482, Woodhead Publishing Ltd, Cambridge, England.

Zong, X. et al., "Structure and process relationship of electrospun bioabsorbable nanofiber membranes", 2002 Polymer 43:4403-4412.

Rosen et al., 1990 "Artificial Nerve Graft Using Collagen as an Extracellular Matrix for Nerve Repair Compared with Sutured Autograft in a Rat Model", Ann Plast Surg 25: 375-87.

Zong, X., "Electrospun fine-textured scaffolds for heart tissue constructs", 2005 Biomaterials 26: 5330-8.

Katta, P. et al., "Continuous Electrospinning of Aligned Polymer Nanofibers onto a Wire Drum Collector", 2004, Nano Lett 4: 2215-2218.

Li, D. et al., "Collecting Electrospun Nanofibers with Patterned Electrodes", 2005 Nano Lett 5: 913-6.

Hagchi, 2012, "Electrospinning of Nanofibers in Textiles", International Journal of Chemoinformatics and Chemical Engineering; Apple Academic Press; 1-139.

Deltamakers. DeltaMaker—An Elegant 3D Printer. YouTube. Jan. 24, 2013. [retrieved on Nov. 13, 2014]. Retrieved from Internet: <http://www.youtube.com/watch?v=3EfxZTI-3B0>.

Kim, K., 2003 "Control of degradation rate and hydrophilicity in electrospun non-woven poly(D,L-lactide) nanofiber scaffolds for biomedical applications", Biomaterials, 24:4977-4985.

Brannon-Peppas, 1997 "Biomaterials—Polymers in Controlled Drug Delivery", Medical Plastics and Biomaterials, Magazine, pp. 1-10.

* cited by examiner

ROBOTIC ELECTROPROSESSING SYSTEM AND METHOD

CROSS-REFERENCE TO RELATED APPLICATIONS

This application is the U.S. national stage application filed under 35 § U.S.C. 371 claiming benefit to International Patent Application No. PCT/US2014/052297, filed Aug. 22, 2014, which is entitled to priority under 35 U.S.C. § 119(e) to U.S. Provisional Patent Application No. 61/869,326, filed Aug. 23, 2013, each of which applications are incorporated by reference herein in their entireties.

BACKGROUND OF THE INVENTION

Electrospun nanofibrous mats and scaffolds are increasingly used for diverse applications, such as for water filtration or tissue engineering. Common laboratory scale electrospinning setups can be built inexpensively with merely a syringe pump, a high voltage supply, and an aluminum foil target. However, these systems are typically limited in the size of possible scaffolds and scaffold geometry they can generate. For example, scaffolds are limited to sizes of only several centimeters (Deitzel et al., 2001, Polymer, 42: 8163-8170). Further, the shape of scaffolds is limited because targets must accommodate a constant spinneret-to-target distance. These systems also require human calibration for each run, and frequent maintenance during spinning (Leach et al., 2011, J Vis Exp, 47: e2494).

Therefore, there is a need in the art for improved electroprocessing systems, including, but not limited to systems suitable for electrospinning and/or electrospraying. The present invention satisfies this unmet need.

SUMMARY OF THE INVENTION

The present invention provides a robotic electroprocessing system. The system comprises a spinneret head; at least three linear actuators connected to the spinneret head; a target; and a motor that drives movement of the linear actuators. The target, the spinneret head and the at least three linear actuators are positioned in an environmentally sealed chamber.

In one embodiment, each of the at least three actuators are connected to a first end of one or more arms, wherein the second end of the one or more arms are connected to the spinneret head. In one embodiment, the arms are connected to the actuators and head using universal joints providing at least two degrees of freedom.

In one embodiment, the head comprises one or more needles capable of being electrified. In one embodiment, the one or more needles are connected via tubing to one or more fluidic pumps located exterior to the chamber. In one embodiment, the chamber further comprises one or more auxiliary electrodes.

In one embodiment, each of the at least three actuators comprises a movable carriage connected to the spinneret head, wherein the carriage moves along the actuator as driven by the motor, thereby moving the spinneret head. In one embodiment, the motor is a stepper motor which turns a screw of the actuator, thereby moving the carriage.

In one embodiment, the chamber provides a controlled isolated environment. In one embodiment, the chamber is devoid of conductive materials which would interfere with an electrical field generated by voltage supplied to the needle.

In one embodiment, the spinneret head moves in three dimensions in order to provide a constant distance along the Z-axis, between the head and the target, while moving along the X or Y axis, thereby allowing for electroprocessing onto targets with surfaces of irregular heights for the production of irregular shaped material. In one embodiment, the head moves at a resolution of less than about 10 μm.

In one embodiment, the target rotates. In one embodiment, the rotation of the target allows for coating of irregular shaped 3-D materials.

In one embodiment, the system further comprises a computing device which controls the movement of the head and environment within the chamber.

The present invention provides a method of manufacturing a material comprising providing a robotic electroprocessing system comprising a spinneret head; at least three linear actuators connected to the spinneret head; a target; and a motor that drives movement of the linear actuators; wherein the target, the spinneret head and the at least three linear actuators are positioned in an environmentally sealed chamber. The method comprises administering a fluid comprising at least one component to be deposited to at least one needle positioned on the head; and producing an electrical field between the needle and the target, thereby depositing the component onto the target.

In one embodiment, the method comprises moving the head in three-dimensions to deposit the component at a desired location of the target. In one embodiment, the method comprises depositing the component onto a surface having irregular heights by moving the head to provide a constant distance along the Z-axis between the head and the target, while moving along the X or Y axis. In one embodiment, the method produces irregular shaped materials.

In one embodiment, the material is biocompatible. In one embodiment, the material is a scaffold for tissue engineering. In one embodiment, the component is chosen from a group consisting of a natural component, synthetic component, and a biological component.

In one embodiment, the generated electrical field and the location of component deposition is not interfered with by the presence of conductive materials within the chamber.

In one embodiment, the method comprises electroprocessing of at least one component and printing of at least one component. In one embodiment, the method comprises electrospinning of at least one component and electrospraying of at least one component.

In one embodiment, the method comprises rotating the target, thereby depositing the component onto a rotating target. In one embodiment, the method coats irregular shaped 3-D materials.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 7, comprising

FIG. 15, comprising

DETAILED DESCRIPTION

Figure 1:
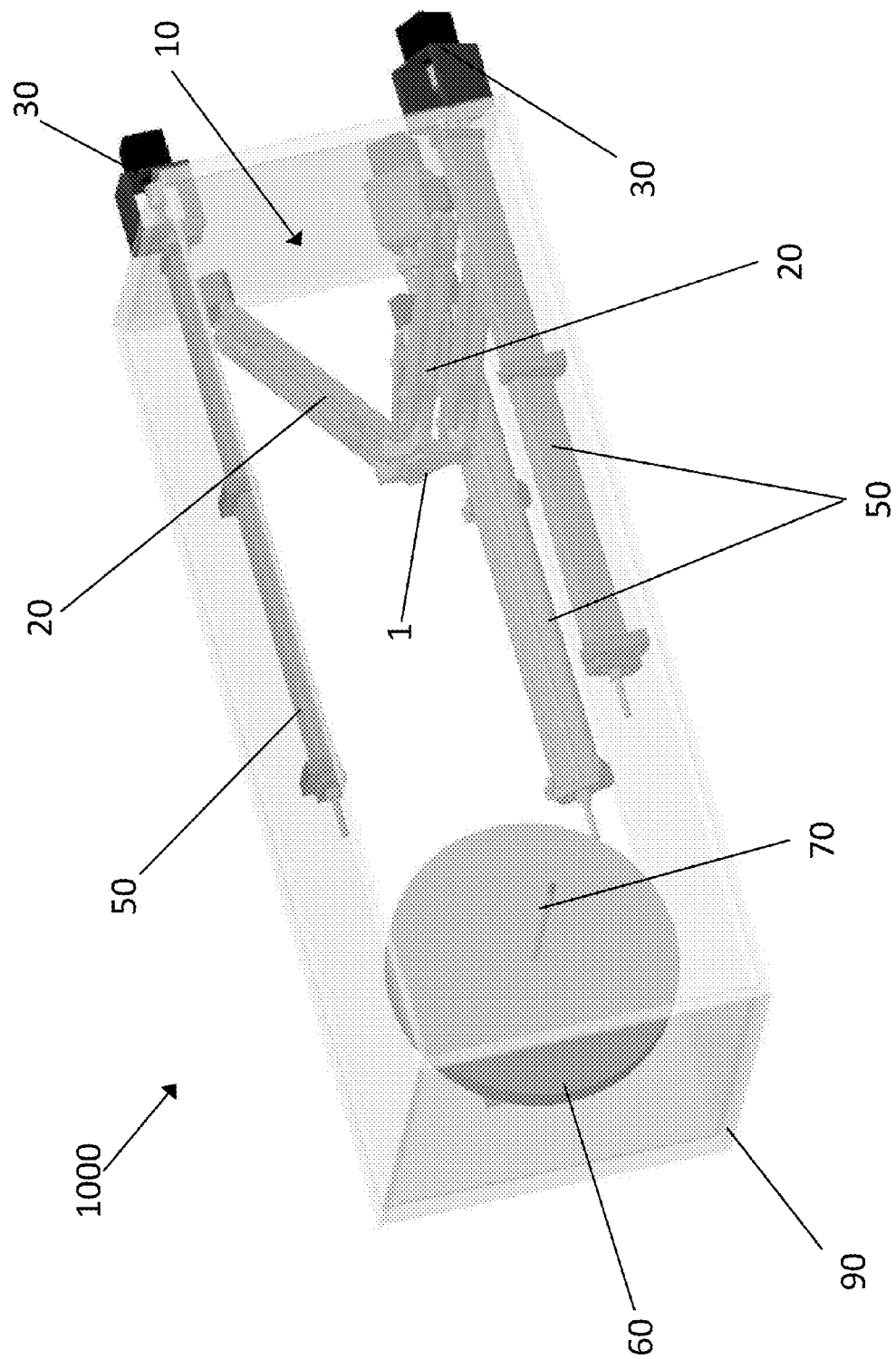
FIG. 1 is a perspective view of an exemplary system of the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed invention.

The term "electroprocessing" shall be defined broadly to include all methods of electrospinning, electrospraying, electroaerosoling, and electrosputtering of materials, combinations of two or more such methods, and any other method wherein materials are streamed, sprayed, sputtered or dripped across an electric field and toward a target. The electroprocessed material can be electroprocessed from one or more reservoirs in the direction of a differently charged substrate. In certain embodiments, the reservoir or target is grounded. In some instances, the electric field from the reservoir to the substrate may not include a ground plane, for example it may be from a +10 kV reservoir to a −5 kV target. The term electroprocessing is not limited to the specific examples set forth herein, and it includes any means of using an electrical field for depositing a material on a target.

As used herein, the term "electrospinning," also known as "electrostatic spinning," includes various processes for forming polymeric fibers including nanofibers and microfibers by expressing a liquid polymeric formulation through a capillary, syringe or similar implement (referred to herein as a flow tube) under the influence of an electrostatic field and collecting the so-formed fibers on a target.

"Electroaerosoling" means a process in which droplets are formed from a solution or melt by streaming an electrically charged polymer solution or melt through an orifice.

As used here, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention includes a robotic system for the enhanced automation, manipulation, and control of electroprocessing in two or three dimensions. Electroprocessing, as used herein, refers to electrospinning, electrospraying, electroaerosoling, electrosputtering, and the like of natural, biologic, or synthetic components, combinations of two or more such methods, and any other method wherein components are streamed, sprayed, sputtered or dripped across an electric field and toward a target.

The system of the invention allows for the fabrication of materials for biological, industrial, or commercial applications. In certain embodiments, the system of the invention produces materials or scaffolds with complex shapes, including materials with ridges, valleys, curves, and the like, which are difficult or impossible to construct using traditional systems. Importantly, the system includes a sealed chamber devoid of any electrical or conductive components which would interfere with the electrical field and eventual material fabrication, while still allowing 2D and 3D robot motion.

The robotic system presented here not only allows for the creation of larger scaffolds, but also presents an ability to alter electroprocessing parameters in real time, enabling researchers to pursue a range of new setup parameters without requiring the purchase of an expensive setup. The system design is particularly amenable for electroprocessing because mechanical linkages can easily isolate electromechanical components from the system, preventing spurious effects on the engineered voltage gradient setup during electroprocessing. By implementing a full three dimensional range of motion, targets can be kept in a single location, allowing easy construction of a sealed environmental chamber with only a single portal to control moving targets.

Electrospinning is an atomization process of a conducting fluid which exploits the interactions between an electrostatic field and the conducting fluid. When an external electrostatic field is applied to a conducting fluid (e.g., a semi-dilute polymer solution or a polymer melt), a suspended conical droplet is formed, whereby the surface tension of the droplet is in equilibrium with the electric field. Electrostatic atomization occurs when the electrostatic field is strong enough to overcome the surface tension of the liquid. The liquid droplet then becomes unstable and a tiny jet is ejected from the surface of the droplet. As it reaches a grounded target, the material can be collected as an interconnected web containing relatively fine, i.e. small diameter, fibers. The resulting films (or membranes) from these small diameter fibers have very large surface area to volume ratios and small pore sizes. A detailed description of electrospinning apparatus is provided in Li et al., 2005, 2005, Biomaterials, 26: 5999-6008; Lelkes et al., 2008, Electrospinning of natural proteins for tissue engineering scaffolding in: Handbook of Natural-based Polymers for Biomedical Applications (Rui L. Reis editor), pp. 446-482, Woodhead Publishing Ltd, Cambridge, England; Zong, et al., 2002 Polymer 43: 4403-4412; Rosen et al., 1990 Ann Plast Surg 25: 375-87; Kim, K., Biomaterials 2003, 24: 4977-85; Zong, X., 2005 Biomaterials 26: 5330-8.

After electrospinning, extrusion and molding can be utilized to further fashion the polymers. To modulate fiber organization into aligned fibrous polymer scaffolds, the use of patterned electrodes, wire drum collectors, or post-processing methods such as uniaxial stretching has been successful. Zong, X., 2005 Biomaterials 26: 5330-8; Katta, P., 2004 Nano Lett 4: 2215-2218; Li, D., 2005 Nano Lett 5: 913-6.

Electrospinning involves the spinning of non-woven fabric of polymer solutions or even polymer melts (like melted nylon) using very high voltages. The solvent is pumped to a needle, called the spinneret, where a very high voltage is applied. If this voltage is high enough, the charges will repel stronger than the surface tension will keep the solution together, and generate Taylor cones. By placing a differently charged target at a defined distance, these cones will start to deposit very thin fibers onto the target. Electrospraying is similar, except the field is so strong that, instead of fibers, the solution will break apart into very small droplets and deposit onto the target as spheres.

The present invention provides a system which overcomes the limitations of standard electroprocessing systems, in which scaffolds created by such devices are generally limited by size and shape. For example, since the distance from the spinneret to the target needs to remain constant, the shapes of resultant scaffolds are often limited to simple structures. The present invention remedies these limitations by utilizing a system having a robot capable of moving in three dimensions. This allows for the creation of scaffolds having complex shapes and sizes. For example, in certain embodiments, the system of the invention allows for the manufacture of three-dimensional structures with branches, grooves, valleys, ridges, and the like.

The design of an electroprocessing system comprising a robot or robotic components is generally complicated by the fact that all grounded sources present in the chamber can become targets for the fibers. Electroprocessing can be affected by electrical fields and environmental factors. Therefore, the present system comprises an isolated chamber which is free of any electronic or conductive system components. Thus, in certain embodiments, the system allows for the use of large and/or complex targets, which would result in arcing and unpredicatable spinning in traditional systems comprising metal or other conductive components. Further, the chamber provides a controlled atmosphere which reduces environmental variables (e.g., temperature and humidity), while enhancing safety by constraining fumes to the chamber.

Figure 2:
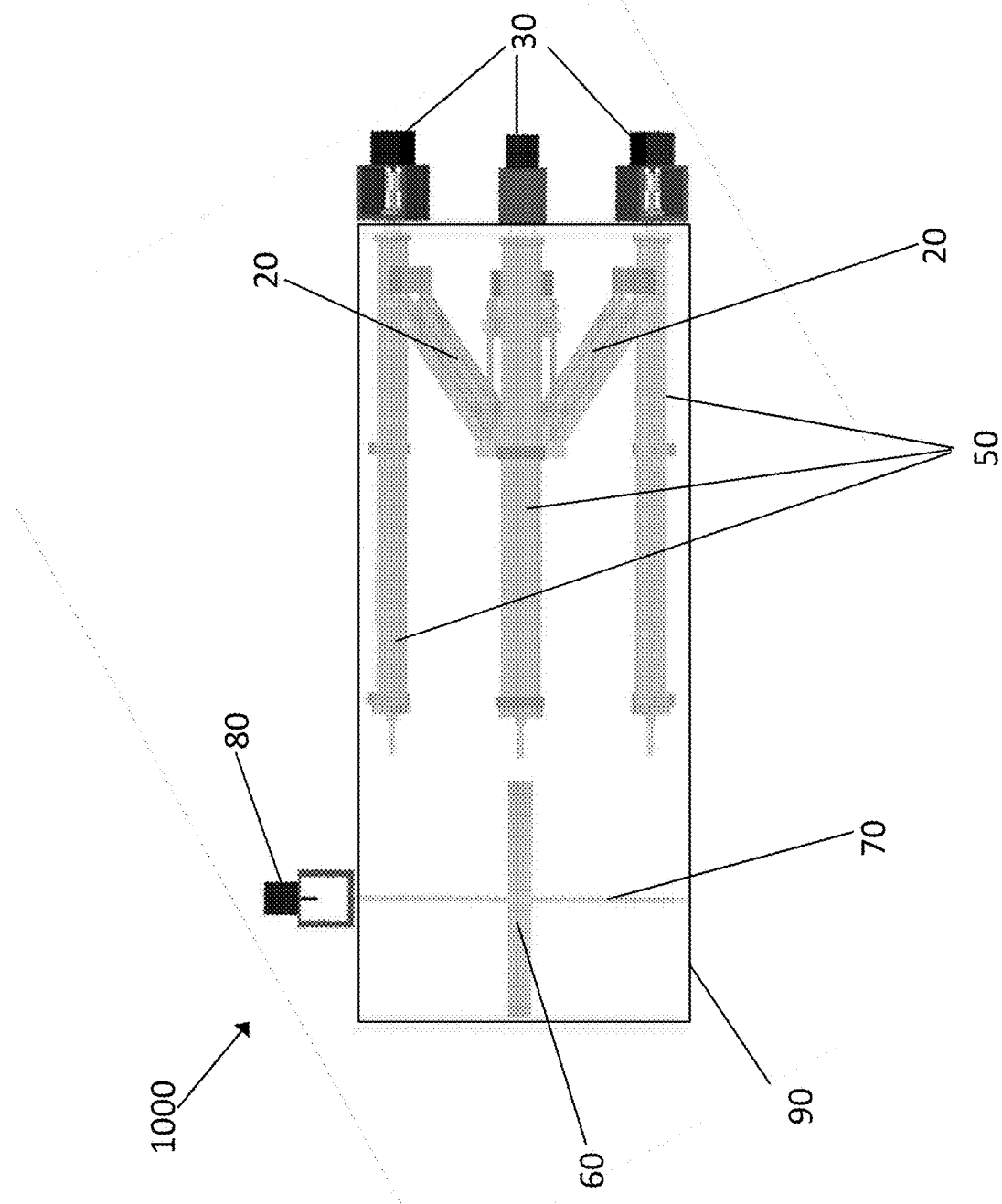
FIG. 2 is a top view of an exemplary system of the invention.

FIG. 1 and FIG. 2 depict an exemplary electrospinning system 1000 of the invention. In one embodiment, system 1000 comprises a sealed chamber 90, robot 10, and target 60. The robot 10 is sealed in the controlled environmental chamber 90 which can be opened for maintenance by an operator. Chamber 90 limits exposure to environmental variables and operator exposure to toxic fumes inside. Environmental control of temperature, humidity, pressure, and atmosphere can be included within chamber 90, or can be manipulated from the outside.

Robot 10 comprises a mobile spinneret head 1 connected to a plurality of parallel linear actuators 50 via one or more arms 20, where actuators 50 are controlled by one or more external drivers 30, which together define the position of mobile spinneret head 1. Spinneret head 1 is capable of moving in all 3 axial directions (X, Y, and Z). For the sake of description, spinneret head 1 and target 60 are separated in the Z direction. The present invention is not limited to any particular number of actuators 50. The present invention is depicted and described herein as comprising three linear actuators 50. However, a skilled artisan would recognize that the invention encompasses the use of any number of linear actuators, such as 4, 5, 6 or 7 linear actuators 50. For example, in certain embodiments, the use of increased number of linear actuators provides more degrees of freedom. For example, in one embodiment, increased numbers of linear actuators allows for three axial directions and three rotational directions.

By utilizing linear actuators 50 composed of polymeric parts for the control of an electrospinning spinneret, very high resolution of control as well as isolation can be achieved. In one embodiment, actuators 5 are made of nonconductive materials, including but not limited to, nonconductive polymers such as nylon, ultra high molecular weight polyethylene (UHMWPE), Polytetrafluoroethylene (PTFE), polypropylene, polyvinyl chloride (PVC), acrylonitrile butadiene styrene (ABS) and polylactic acid (PLA). This ensures that actuators 50 do not interfere with the electrical field during use.

In one embodiment, the system comprises three linear actuators 50 mounted on the corners of an equilateral triangle in the XY plane (actuators 50 oriented in the Z direction), creating a shape as an equilateral triangular pyramid when head 1 is the apex. Each linear actuator 50 is connected to spinneret head 1 by an arm 20 mounted with 2D-universal-joints 24 at each end. By extending linear actuators 50, the height of arms 20 are altered, achieving three-dimensional (XYZ) control of spinneret head 1. The position of linear actuators 50 can be controlled by any suitable mechanism, including, but not limited to, a belt, pneumatics, or by a screw.

Figure 3:
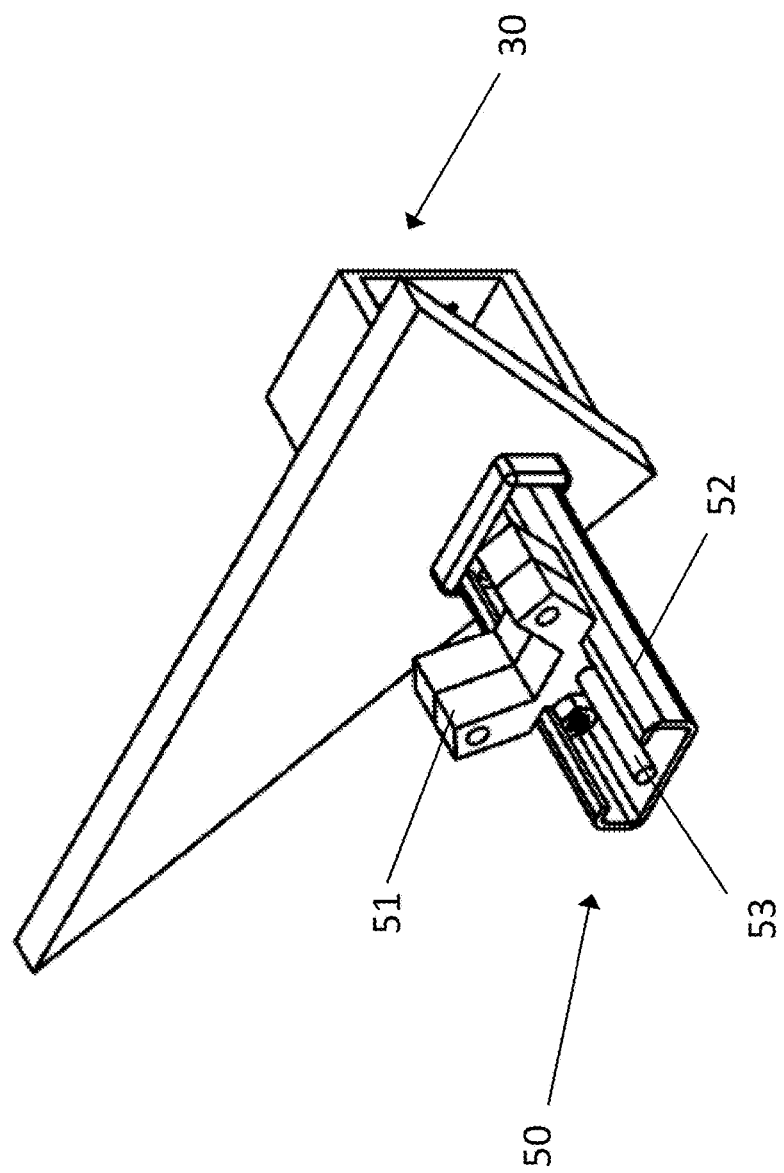
FIG. 3 is an image depicting a linear actuator of an exemplary system of the invention.
Figure 4:
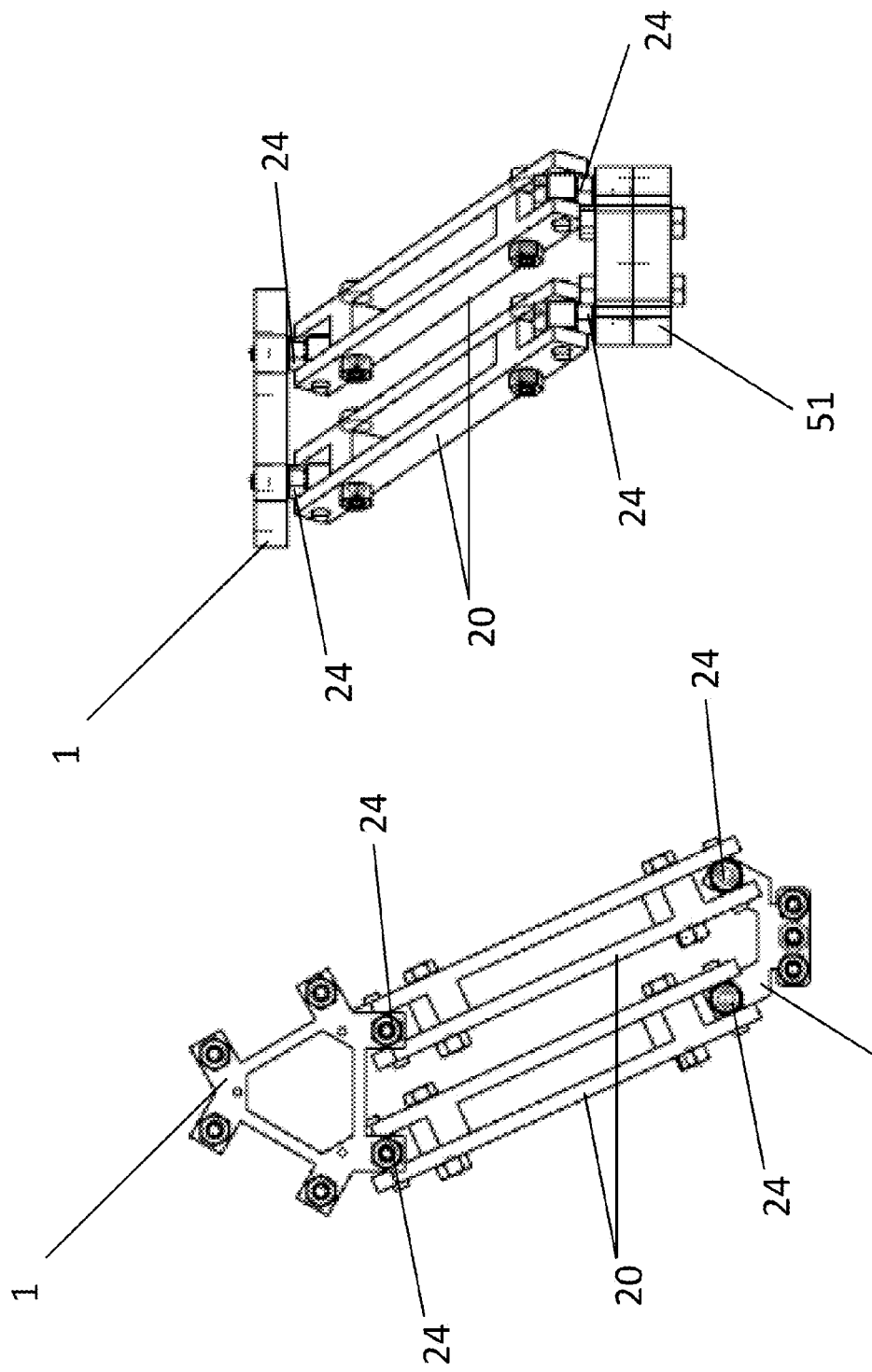
FIG. 4 is a set of images depicting a top view (left) and perspective view (right) of a spinneret head connected to the carriage of a linear actuator by two arms.

For example, as depicted in FIG. 3, in one embodiment, each linear actuator 50 comprises a carriage 51, a guide channel 52 and a screw 53. The carriage 51 comprises an immobilized nut which rides along screw 53. Guide channel 52 holds carriage 51, and in certain embodiments, is made of UHMWPE, or other suitable non-conductive material. In one embodiment, screw 53 is made of nylon, or other suitable non-conductive material. In certain aspects, screw 53 does not travel up and down on its own. Rather it rotates, as driven by an external driver 30, which thereby moves the carriage up and down. In certain embodiments, actuator 50 comprises one or more locked nuts that prevent screw 53 from being pulled up or down. This allows screw 53 to push carriage 51, rather than bend when under pressure of the motor of driver 30. Attached to the carriage is universal joint 24, which connects carriage 51 to arm 20. In certain embodiments, where greater than three linear actuators 50 are used, carriage 51 may be connected to arm 20 via a ball joint. For example, in one embodiment, six linear actuators 50 are used, where each is connected to arm 20 via a ball join, which provides more degrees of freedom for the movement of the robot. In one embodiment, actuator 50 comprises one or more brackets which prevent guide channel 52 from twisting or bending.

In certain embodiments, each linear actuator 50 is connected to head 1 by a plurality of arms 20. For example, in certain embodiments, the use of two or more arms 20 per actuator 50 improves the movement accuracy of head 1. The universal joint provides two degrees of freedom, effectively allowing head 1 to move in a sphere around the joint. The intersecting spheres of the linear actuators 5 thus forms a point. By moving each carriage 51 of actuators 50, head 1 position is changed.

Resolution of robot 100 is determined by the resolution of the positioning linear actuators 50, which is governed by exterior driver 30, connected to each linear actuator 50, as depicted in FIGS. 1-3 and 5. In certain embodiment, driver 30 comprises a motor 31 to adjust the positioning of linear actuators 50. For example, in one embodiment, robot 10 uses a 20-turns-per-inch threaded rod driven by a 200-steps-per-revolution brushless motor enabling 1/4000 steps per inch resolution when moving in the Z direction (approximately 6 micron). In other embodiments, resolution can be improved up at 16 times by the application of microstepping through complex motor control (sub micron resolution). Resolution in other directions may be even finer, where exact values depend on the arm angles.

Figure 5:
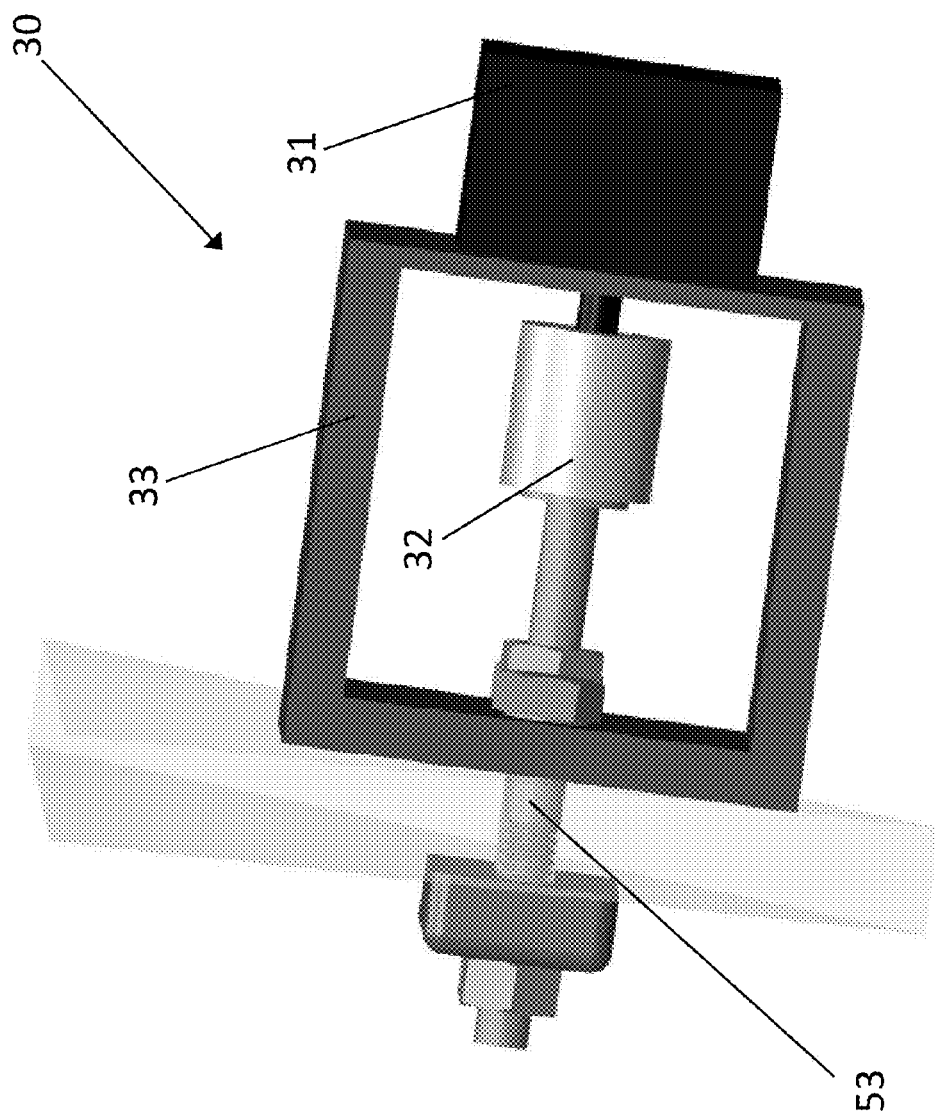
FIG. 5 is an image depicting an external driver of an exemplary system of the invention.

Another exemplary driver 30 of the invention is depicted in FIG. 5. In one embodiment, motor 31 is a stepper motor connected to screw 53, which travels from driver 30 into chamber 90 and into linear actuator 50. In one embodiment the stepper motor is a 3.7V motor, with 200 steps per turn of the screw. Motor 31 is in communication with to screw 53, such that motor steps are translated to screw turns. For example, in certain embodiments, driver 30 comprises a shaft 32 which couples motor 31 to screw 53. In one embodiment, driver 30 comprises a brace 33 connected to chamber 90 and onto which motor 31 is mounted. In certain embodiments, a fast, weak motor may be used, due to the large mechanical advantage of the screw.

Spinneret head 1 can accommodate one or more blunt tip needles for electroprocessing purposes. Any gauge of needle may be used. Each needle is connected to a tube, which is fed out of the chamber 90 through a feed hole, to an external syringe pump. The tubing may be made of any suitable material, including but not limited to polyetheretherketone (PEEK) or silicone. The tubing is narrow to reduce dead space, and removes the pump from chamber 90, and thus reduces any effect it might have on electrostatic fields in chamber 90. In certain embodiments, chamber 90 comprises one or more metal bolts penetrating the back wall which are electrified up to tens of kilovolts and connected by wire to the needle of spinneret head 1.

Figure 6:
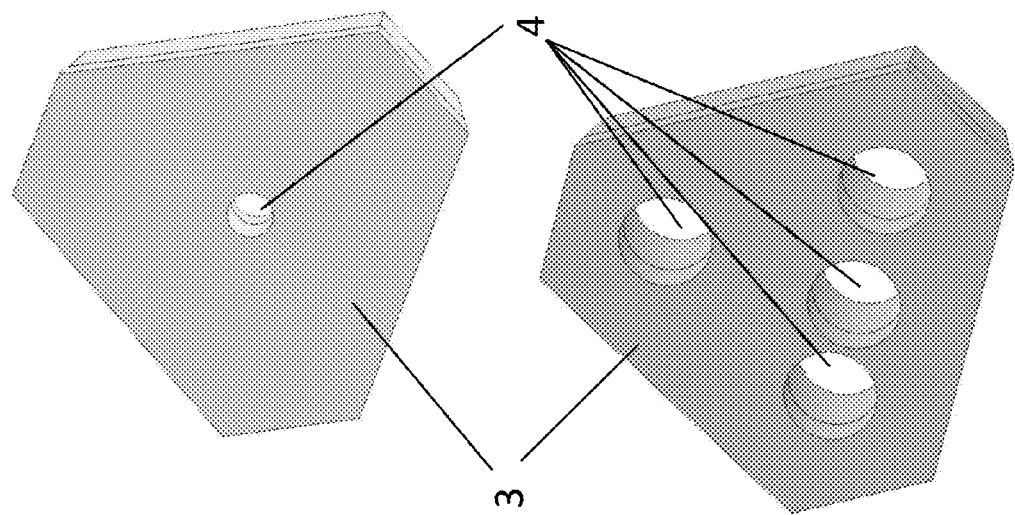
FIG. 6 is an image depicting a spinneret head and two different head inserts of an exemplary system of the invention.
Figure 6:
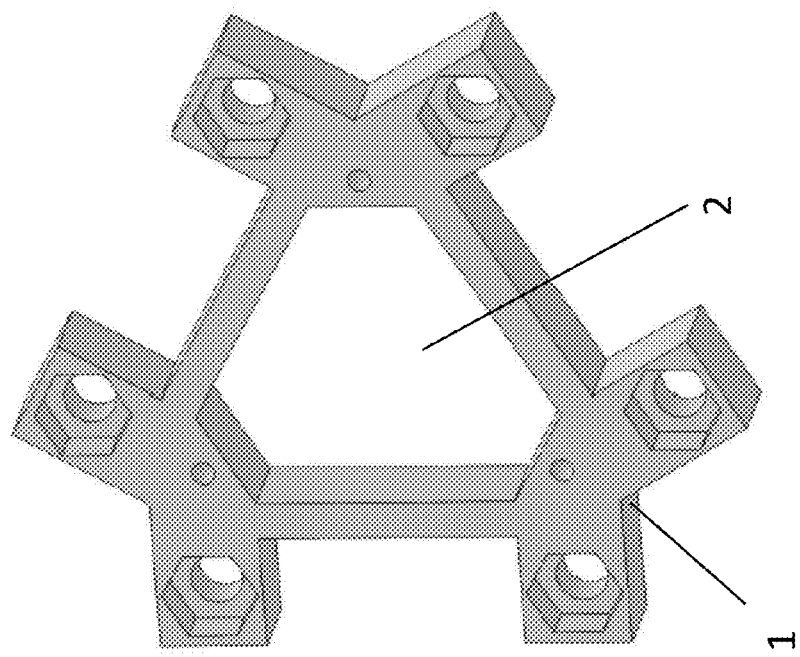

An exemplary spinneret head 1 is depicted in FIG. 6. In one embodiment spinneret head 1 comprises one or more needles removably or permanently affixed to head 1. Head 1 may also comprise a hoop or other auxiliary electrodes attached to the head. In certain embodiments, system 1000 comprises multiple working needles on the single robot head. In one embodiment, head 1 may comprise a recess 2 for insertion of a removable needle holder or head insert 3. Head insert 3 may comprise one or more ports 4 used for a particular application. For example, FIG. 6 depicts two different types of inserts 3, each having a different number, location, and size of ports 4 through which various needles, fluid supplies, air supplies, and the like, may be inserted. The present invention is not limited to the number, location, or size of ports 4, or the arrangement of needles, supplies, and the like, inserted into ports 4 of head 1. Thus, in certain embodiments, head 1 allows for the insertion of various different types of inserts 3, depending on the application desired.

Spinning multiple fibers normally requires needles to be positioned around a rotating target so the fibers and electric fields will not interact during spinning. This greatly limits target geometry. In contrast, by having a robot that can move in many dimensions, combined with computer controlled voltage sources and pumps, the present system allows for multiple fibers to be spun from the same head simply by switching the active needle every few microns of deposition and allowing the robot to move back and forth between the appropriate spinning positions. This is not realistically possible in a manual setup simply because the manual interaction would require not only a great deal of effort, but the time it would take between setups may cause the solvents to evaporate too much.

In certain embodiments, one or more of the needles may be used for electrospinning, electrospraying, electrosputtering, printing, or the like. That is, not all needles need to be used exclusively for the same purpose. For example, in one embodiment, a first needle is used to electrospin a first component of a material while a second needle is used to electrospray a second component of a material. Similarly, in one embodiment, a needle may be used to directly print a component at the target or resulting material. This allows the present system to produce complex materials and scaffolds having spatially distinct features, including gradients. In certain embodiments, along with electrospinning needle, head 1 or insert 3 comprises ports or needles used for 3-D printing, inkjet printing, air-brushing, or spraying of desired compounds onto or into electrospun materials. For example, in certain embodiments, head 1 or insert 3 comprises a piezoelectric-driven atomizer or air atomizer which may be used to deposit droplets onto or into the electrospun materials.

The present invention allows access to diverse electrospinning or electrospraying fluids and varying voltages in real time without compromising the environmental integrity of the box as each feed port can be sealed easily. In certain embodiments, the system comprises one or more feed ports as needed for various power supplies, tubing, and the like. Feed ports may be sealed with an appropriate material, for example silicone, to isolate the chamber environment.

System 1000 comprises a target 60, on which electroprocessed material is deposited. In certain embodiments, target 60 comprises a conductive surface that is electrified or grounded. As shown in FIG. 1 and FIG. 2, target 60 is constructed at the far end of the chamber 90 (for example, several centimeters in the Z direction away). In one embodiment, target 60 is either grounded, or electrified to a potential different from the needles of spinneret head 1 to induce a controlled electrical field. For example, the system may comprise a positive voltage biased needle, and a negative biased or grounded target. The electrospinning field is generated through the control of target and needle voltages, and can be further manipulated by including additional auxiliary electrodes, for example, an electrified hoop, between the two, or four plates like in a televisions cathode ray tube. A particular benefit of the presently described system is the ability to place one or more additional electrodes throughout chamber 90 to produce a desired electrical field design. As chamber 90 is devoid of conductive components, there is no risk of electroprocessing onto system components instead of the target.

In one embodiment, target 60 is fixed in place by a polymer or glass rod 70 crossing chamber 90 in the Y direction. In one embodiment, rod 70 is a stationary rod connected to a rectangular flat target 60. In another embodiment, rod 70 is rotatable, which is rotated by a motor 71 attached outside of chamber 90, and is connected to a cylindrical or odd shaped three dimensional target 60. This can be used for targets shaped after internal organs such as a heart, liver or kidney. In certain aspects, rod 70 rotates with controlled speed by target motor 80, up to scores of thousands RPM. It should be appreciated that the present invention uniquely allows for target 60 to be temporarily stationary or moving, and to be any shape. The elected shape and degree of movement will be application dependent.

Electroprocessing onto awkwardly shaped targets is less common because spinneret-target distance must be kept near constant. With a computer controlled robotic spinneret, the needle of head 1 can move to accommodate changing target shapes and distances as rod 70 rotates the target 60. In certain embodiments, rod 70 and screw 53 actuator 50 are the only pieces that have to be able to spin and penetrate chamber 90. The fitting is kept tight and vacuum grease is used to seal any hole.

All parts within chamber 90 are made of non-conductive materials to reduce any obfuscation of the engineered voltage gradient between the needles, targets, and any auxiliary electrodes. Linear actuator 50 is constructed of non-conductive material, and driver 30 for actuator 50 is located outside of chamber 90, at sufficient distance from the electrospinning field. As the main advantage and innovation of the delta-robot design for electrospinning, three-axis robotic control is realized without any floating electronic components or the inclusion of any of the robotic electronics inside the spinning chamber.

In one embodiment, the system comprises a fluidic pump which holds one or more solutions to be delivered to the needles of robot 10 for electroprocessing. The present invention is not limited to any particular type of fluidic pump. Exemplary fluidic pumps include, but are not limited to, syringe pumps, peristaltic pumps, pneumatic fluidic delivery pumps, and the like. For example, in certain embodiments, the syringe pump may hold about 0.5 mL to about 100 mL of solution. In one embodiment, the syringe pump delivers the solution at a rate of about t 0.1 to about 1000 microliters/min, more preferably about 1 to about 250 microliters/min. In certain embodiments, where multiple needles are used simultaneously, the pump may deliver the solution at increased flow rates to supply the multiple needles.

In one embodiment, the system of the invention comprises a computing device. In one embodiment, the computing device controls one or more of the system components. For example, in certain embodiments the computing device controls temperature, humidity, atmospheric pressure, electrode voltage, electrical field strength, electrical field configuration, feed rate of the solution, and the 2-D or 3-D positioning of the target and spinneret head. For example, the computing device may be in communication with the motors of the system to alter the 3-D positioning of the spinneret head and with voltage sources to control the charge of the needles and target. For example, in certain embodiments, head motion is controlled in real time, for example through computer control of an AT-Mega microprocessor which also controls environmental parameters and electrode voltages. In certain embodiments, the system comprises a heating element, cooling element, humidifier, dehumidifier, vacuum pump, and combinations thereof, in order to control the chamber environment. In one embodiment, the computing device communicates with such components to alter the temperature, humidity, and the like as needed or desired.

The computing device may communicate with one or more system components via wired connection or wirelessly. In one embodiment, the computing device comprises a software platform for communication with the system components. The software platform includes a graphical user interface (GUI) for monitoring and modulating system or user information, such as robot function, robot position, target position or rotation, feed rate, voltage, electrical field strength, 2-D cross-sectional views of electric field strength, pressure, temperature, humidity, 3-D position, battery power level, and the like In certain embodiments, wireless communication may be via a wide area network and may form part of any suitable networked system understood by those having ordinary skill in the art for communication of data to additional computing devices, such as, for example, an open, wide area network (e.g., the internet), an electronic network, an optical network, a wireless network, a physically secure network or virtual private network, and any combinations thereof. Such an expanded network may also include any intermediate nodes, such as gateways, routers, bridges, internet service provider networks, public-switched telephone networks, proxy servers, firewalls, and the like, such that the network may be suitable for the transmission of information items and other data throughout the system.

Data transfer can be made via any wireless communication may include any wireless based technology, including, but not limited to radio signals, near field communication systems, hypersonic signal, infrared systems, cellular signals, GSM, and the like. In some embodiments, data transfer is conducted without the use of a specific network. Rather, in certain embodiments, data is directly transferred to and from the system components via systems described above.

As would be understood by those skilled in the art, the system components, including the computing device, may be wirelessly connected to the expanded network through, for example, a wireless modem, wireless router, wireless bridge, and the like. Additionally, the software platform of the system may utilize any conventional operating platform or combination of platforms (Windows, Mac OS, Unix, Linux, Android, etc.) and may utilize any conventional networking and communications software as would be understood by those skilled in the art.

To protect data, an encryption standard may be used to protect files from unauthorized interception over the network. Any encryption standard or authentication method as may be understood by those having ordinary skill in the art may be used at any point in the system of the present invention. For example, encryption may be accomplished by encrypting an output file by using a Secure Socket Layer (SSL) with dual key encryption. Additionally, the system may limit data manipulation, or information access. Access or use restrictions may be implemented for users at any level. Such restrictions may include, for example, the assignment of user names and passwords that allow the use of the present invention, or the selection of one or more data types that the subservient user is allowed to view or manipulate.

The computing device may include, for example, laptops, desktops, tablets, smartphones or other wireless digital/cellular phones, wrist watches, televisions or other thin client devices as would be understood by those skilled in the art. The computing devices may include at least one processor, standard input and output devices, as well as all hardware and software typically found on computing devices for storing data and running programs, and for sending and receiving data over a network, if needed.

The software may include a software framework or architecture that optimizes ease of use of at least one existing software platform, and that may also extend the capabilities of at least one existing software platform. The software provides applications accessible to one or more users to perform one or more functions. Such applications may be available at the same location as the user, or at a location remote from the user. Each application may provide a graphical user interface (GUI) for ease of interaction by the user with information resident in the system. A GUI may be specific to a user, set of users, or type of user, or may be the same for all users or a selected subset of users. The system software may also provide a master GUI set that allows a user to select or interact with GUIs of one or more other applications, or that allows a user to simultaneously access a variety of information otherwise available through any portion of the system. Presentation of data through the software may be in any sort and number of selectable formats. For example, a multi-layer format may be used, wherein additional information is available by viewing successively lower layers of presented information. Such layers may be made available by the use of drop down menus, tabbed pseudo manila folder files, or other layering techniques understood by those skilled in the art.

The software may also include standard reporting mechanisms, such as generating a printable results report, or an electronic results report that can be transmitted to any communicatively connected computing device, such as a generated email message or file attachment. Likewise, particular results of the aforementioned system can trigger an alert signal, such as the generation of an alert email, text or phone call, to alert a user.

The present invention provides methods of manufacturing materials such as, 2-D or 3-D scaffolds, fabrics, mats, and the like. Exemplary materials produced by the system and method of the invention may be used in a variety of biological, tissue engineering, regenerative medicine, industrial, or commercial applications.

The method comprises the electroprocessing of any suitable natural, biologic, or synthetic components. In certain embodiments, the method comprises electroprocessing of a combination of natural, biologic, or synthetic components. Electroprocessing is broadly interpreted to include methods of electrospinning, electrospraying, electroaerosoling, and electrosputtering of materials, combinations of two or more such methods, and any other method wherein components are streamed, sprayed, sputtered or dripped across an electric field and toward a target.

As described herein, the present invention allows for the production of materials of unique size and shape. For example, it is demonstrated herein the 3D movement of the spinneret head of the presently described system produces larger scaffolds than similar prior systems. For example, using a circular target, scaffolds of up to 14.5 cm or greater in diameter is created. In certain embodiments, scaffold sheets of up to 14.5 cm×80 cm or greater are created. The use of complex targets or larger robots can vastly increase scaffold size. Further, the system allows for the production of large circular scaffolds and irregular shaped materials that are difficult or impossible to produce otherwise. Further it is demonstrated herein that the 3-D movement of the spinneret head in order to maintain a constant separation distance between the target and head provides for more even spinning and consistent fiber geometry. Thus, the present methods allow for the formation of electroprocessed scaffolds or mats having complex geometries with consistent fiber geometry. In certain embodiments, the method allows for the formation of electrospun scaffolds or mats having regions or layers of differing fiber type or fiber geometry, by varying the separation distance between the target and the spinneret.

In one embodiment, the method of the invention comprises formation of a de novo material as a result of electroprocessing of components on to a surface. For example, components may be deposited onto a surface and then removed from the surface, resulting in the finished material. In another embodiment, the method comprises coating of a substrate with one or more electroprocessed components. For example, the present invention provides for 3-D control of the spinneret head, thereby allowing for the coating of irregular shaped substrates. For example, as it is generally required for the Z-distance between the target substrate and spinneret head to remain constant, the present method allows for the robotic spinneret head to change its Z-position to allow for a constant distance, during the coating of different areas of the irregularly shaped substrate. For example, if the substrate has a ridge, as the X-Y position of the head is moved to coat the substrate, the Z-position of the head is continually altered as appropriate such that the distance between the substrate and head remains constant.

In one embodiment, synthetic components comprise synthetic polymers. Such polymers include but are not limited to the following: poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly (ethylene glycol), poly(methacrylic acid), polylactides (PLA), polyglycolides (PGA), poly(lactide-co-glycolides) (PLGA), polyanhydrides, plyanilines, polypyrroles, and polyorthoesters or any other similar synthetic polymers that may be developed and electrospun or electrosprayed using the method and system of the invention. Synthetic materials shall also include copolymers and blends, and any other combinations of the forgoing either together or with other polymers generally. The use of these polymers will depend on given applications and specifications required. The polymers may have any molecular structure including, but not limited to, linear, branched, graft, block, star, comb and dendrimer structures. In certain embodiments, the synthetic material used in the invention is biocompatible. For example, a more detailed discussion of these polymers and types of polymers is set forth in Hagchi, 2011, Electrospinning of Nanofibers in Textiles, CRC Press and Brannon-Peppas, Lisa, "Polymers in Controlled Drug Delivery," Medical Plastics and Biomaterials, November 1997, each of which are herein incorporated by reference in their entireties.

In one embodiment, the biological component used in the method of the present comprise biopolymers, such as extracellular matrix proteins, which include but are not limited to collagen, fibrin, elastin, gelatin, fibrinogen, thrombin, laminin, chondroitin sulfates, heparins, hyaluronic acid, alginate, dextran, pectin, and chitosan. In certain embodiments, the biological component comprises amino acids, peptides, proteins, carbohydrates, lipids, nucleic acids, glycoproteins, minerals, lipoproteins, glycolipids, glycoaminoglycans, and proteoglycans. In certain embodiments, the natural or biological component of the invention is derived from plant products. For example, the component may comprise plant material including, but not limited to soy protein and corn zein.

In one embodiment, a solution to be electroprocessed is formed. Formation of the solution may be done in any suitable method known in the art. One method involves dissolving the desired component in an appropriate solvent. This process can be accomplished in a syringe assembly or it can be subsequently loaded into a syringe assembly. Another method involves purchasing commercially available polymer solutions or commercially available polymers and dissolving them to create polymer solutions. For example, poly(ethylene oxide) (PEO) can be purchased from Sigma (Sigma, St. Louis, Mo.), poly-L-lactide (PLLA) can be purchased from DuPont (Wilmington, Del.), poly(lactide-co-glycolide) can be purchased from Ethicon (Somerville, N.J.). Additional polymer scaffold components of the invention, such as cells and biomolecules, are also commercially available from suppliers.

The solvent can be any solvent which is capable of dissolving the desired component. Typical solvents include a solvent selected from N,N-Dimethyl formamide (DMF), tetrahydrofuran (THF), methylene chloride, dioxane, ethanol, hexafluoroisopropanol (HFIP), chloroform, glacial acetic acid, water, and combinations thereof.

In one embodiment, the solution can optionally contain a salt which creates an excess charge effect to facilitate the electrospinning process. Examples of suitable salts include $NaCl$, $KH_2PO_4$, $K_2HPO_4$, $KIO_3$, $KCl$, $MgSO_4$, $MgCl_2$, $NaHCO_3$, $CaCl_2$ or mixtures of these salts.

In certain embodiments, the method comprises designing and administering an electrical field resulting in the electroprocessing of the biological or synthetic components of the solution. As described elsewhere herein, the method allows for the design of electrical field based upon the electrical field generated by one or more electrodes placed throughout the chamber. The nonconductive components within the system chamber, allow for the design of predictable electrical fields that would otherwise be impossible due to interference created by traditional electromechanical robotic components.

The electric field created in the electrospinning process preferably is in the range of about 5 to about 100 kilovolts (kV), more preferably about 10 to about 50 kV.

In certain embodiments, the method comprises electroprocessing of one or more solutions. For example, in certain embodiments, the robotic head of the system comprises more than one needle, thereby allowing for the controlled deposition of fibers or droplets from each needle, as controlled by the user. The present invention allows for seamless switching between different solutions and simultaneous adjustment of the 3D positioning of the head, as appropriate or needed for the electroprocessing of the particular solution.

The feed rate of the conducting fluid to the spinneret preferably is in the range of about 0.1 to about 1000 microliters/min, more preferably about 1 to about 250 microliters/min.

As described elsewhere herein, the system comprises one or more needles or electrodes affixed to the robotic spinneret head. As such, in certain embodiments, the method of the invention comprises varying the 3-D positioning of the spinneret head in order to vary the lateral (XY) positioning as well as the distance between the head and target (Z). The distance between the head and target can be any distance which allows the solvent to essentially completely evaporate prior to the contact of the polymer with the target. In an exemplary embodiment, this distance can vary from 1 cm to 25 cm. Increasing the distance between the head and the target generally produces thinner fibers.

In certain embodiments, the method comprises rotating the target, which in certain embodiments produces tubular materials. In one embodiment, rotation of the target provides for the production of materials with aligned fibers. In electrospinning cases where the target is rotated, a rotating mandrel, or rod, is mechanically attached to a motor, often through a drill chuck. In an exemplary embodiment, the motor rotates the rod at a speed of between about 1 revolution per minute (rpm) to about 500 rpm. In an exemplary embodiment, the motor rotation speed of between about 200 rpm to about 500 rpm. In another exemplary embodiment, the motor rotation speed of between about 1 rpm to about 100 rpm.

As described elsewhere herein, in certain embodiments, the one or more needles affixed to the robotic head need not all be used for one type of processing or deposition. For example, in certain embodiments, the method comprises electrospinning using a first electrode and electrospraying using a second needle. In one embodiment, the method comprises direct printing of compounds of interest (e.g., bioactive molecules, growth factors, etc.) from one or more of the needles. In certain embodiments, the method comprises deposition of compounds of interest onto or into a material via the atomization of a solution. For example, in certain aspects, the method comprises using an airbrush-based head to paint compounds of interest (e.g., bioactive molecules, growth factors, etc.) onto the electroprocessed material. This combinatorial approach provided by the present invention can greatly expand traditional fabrication techniques. For example, it has been demonstrated that gradients of growth factors and alignment of matrix can both act to guide cells. Unfortunately, outside of microfluidic test beds, these abilities are never, or very rarely, applied together. This is because aligned matrix production has been incompatible with most gradient laying techniques.

However, the present invention allows for the production of such complex materials, which were difficult or impossible to produce otherwise. For example, in one embodiment, the method comprises producing aligned fibers, for example by spinning the target, followed by electrospraying or printing a carefully constructed gradient of a drug or other desired compound, by varying the spray time along the objects circumference, thus enabling these two methods to be combined in an automated fashion. Such materials would be difficult to produce using a manual setup. For example, in a system comprising simultaneous electrospraying and electrospinning setup, the target can be rotated to produce aligned fibers from the electrospinning set up while the electrospraying pump, containing the desire drug or compound, has a variable pump rate to provide a gradient as the scaffold becomes thicker. However, the direction of fiber alignment and gradient are orthogonal, fibers are aligned circumferentially while the drug is graded radially. It is thus difficult to provide aligned fibers and the gradient in the same direction.

In certain embodiments, the method of the invention comprises providing the system described herein with instructions relating to spinneret position, target position, temperature, humidity, pressure, feed rate of solution, electrical field strength, electrical field configuration, and the like. For example, in one embodiment, the method comprises programming the system, using system hardware and software, to provide the optimal conditions to produce the material of interest.

In one embodiment, the method comprises providing the system with the geometry of the target surface. For example, the topography of the surface can be provided to the computing device of the system, such that the system may adjust, via the 3-D motion of the spinneret head, for the contours, curves, ridges, valleys, and the like of the target surface.

In one embodiment, a point cloud is manually generated of the target surface. For example, the robot is driven across the surface, and one or more points across the surface are recorded by a suitable software program. The points are then interpolated to provide a surface where spinning paths can then be created. This method is useful when the target object is not predetermined and when it may not be suitable or desired to first create a model of the target. In certain embodiments, if a model of the target object exists, for example in STL format, any suitable CAM programs can develop a path. In one embodiment, MRI, CT, or other suitable imaging technique, is used to develop a 3-D model. A target can be generated that matches the geometry of the model, for example using a rapid prototyper such as a 3D printer. The target along with the model can then be used generate a spinning path along the target surface.

In one embodiment, the invention provides methods of forming biocompatible scaffolds for use in biological, tissue engineering, or regenerative medicine applications. For example, in certain embodiments, the invention provides for forming a biocompatible scaffold that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

The scaffold may be formed in any number of desirable configurations to satisfy any number of overall system, geometry or space restrictions. For example, as described herein, the present invention allows for the production of scaffolds with complex size and shape, including scaffolds with curves, ridges, valleys, branches, and the like. For example, in the use of the scaffold for branched airways, bladder, urethra, valve, or blood vessel reconstruction, the scaffold may be shaped to conform to the dimensions and shapes of the whole or a part of the tissue. The scaffold may be shaped in different sizes and shapes to conform to the organs of differently sized patients. The scaffold may also be shaped in other fashions to accommodate the special needs of the patient.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Delta-Style Robot for Electrospinning from Rapid Prototyped Parts

Presented herein is a 3D delta-style electrospinning robot constructed mostly from plastic parts generated in a simple 3D printer.

All custom parts were CAD designed in SolidWorks and then created using a MarkerBot 3D printer (PrintrBot), with Acrylonitrile Butadiene Styrene (ABS) filament. Polyethylene channeling and nylon-threaded rod were purchased from Grainger (Lake Forest, Ill.), and stepper motors, drivers, and Arduino Mega were purchased from Pololu (Las Vegas, Nev.).

Figure 7A:
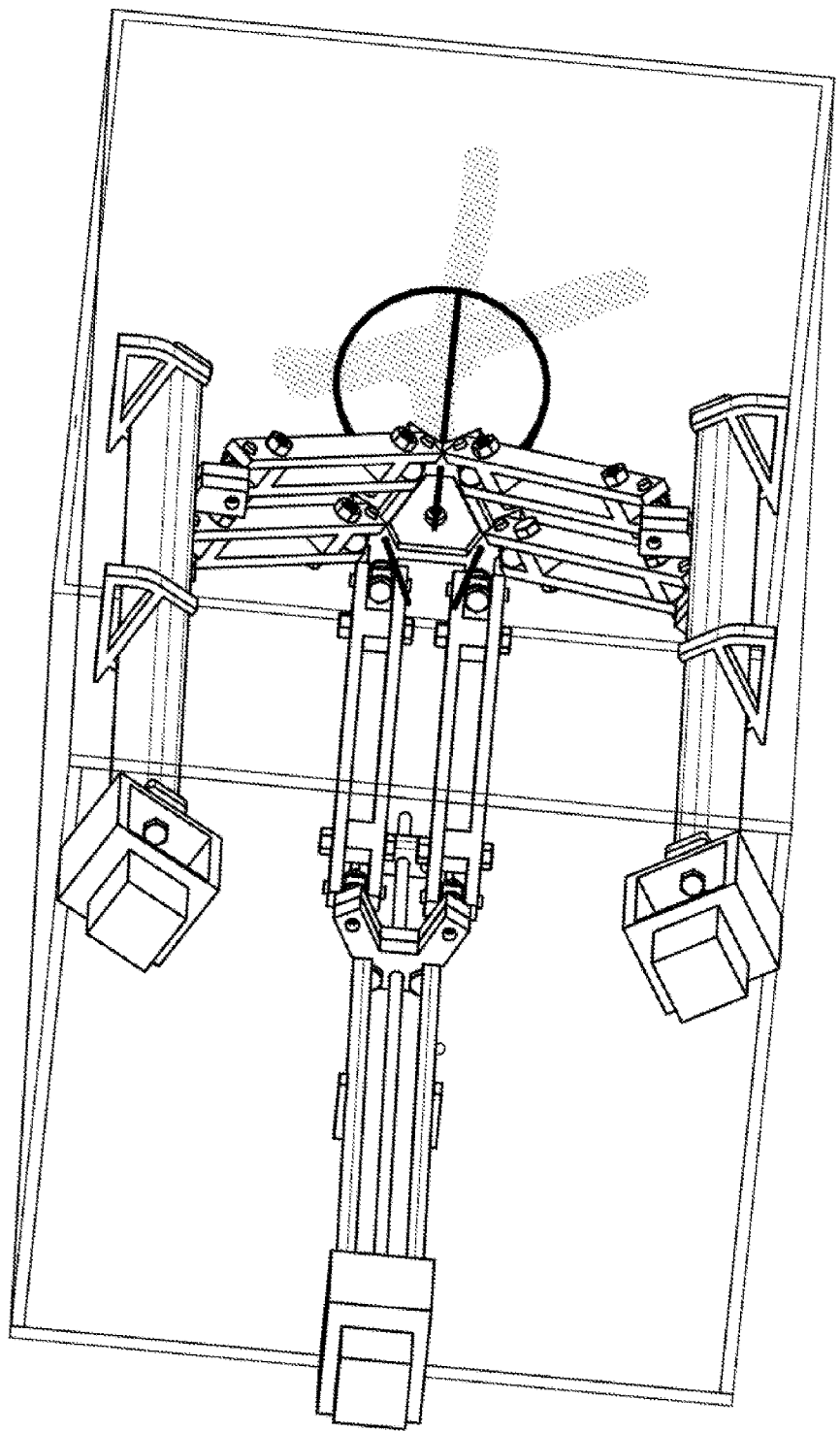
FIG. 7A and FIG. 7B, is a set of images depicting a top view (FIG. 7A) and a side view (FIG. 7B) of a manufactured electrospinning system.
Figure 7B:
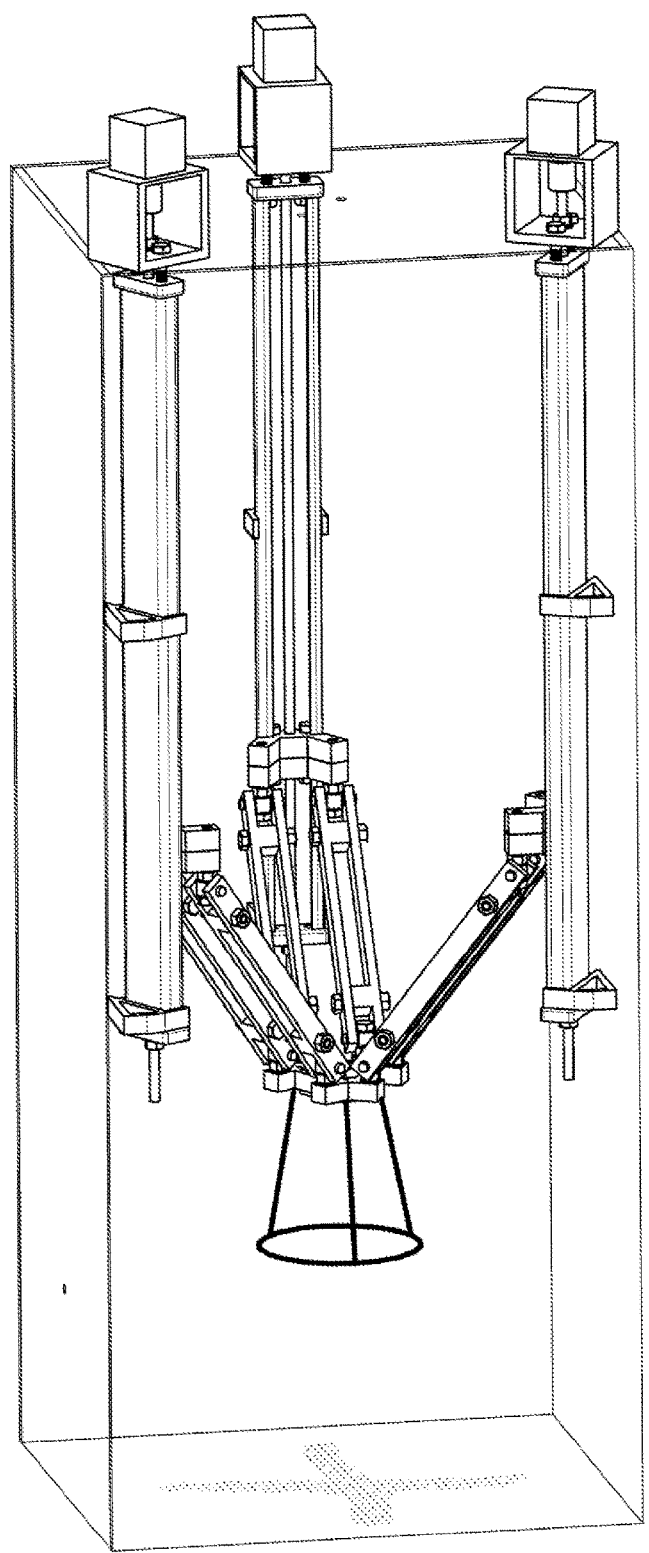

The robot was positioned within a polycarbonate chamber with very minimal pores, present only for voltage and solution lines. The manufactured robot is constructed only with plastic: 3D-printed ABS, manufactured nylon and polyethylene. The trajectory is calculated in Matlab 2012a, and the robot is controlled though Arduino Mega running Marlin software. The setup allows operators to control spinning parameters without risk of injury and enables more complex spinning parameters. The delta robot design allows a very large range of motion without including any control electronics in the chamber. FIG. 7 depicts a top view (FIG. 7A) and side view (FIG. 7B) of the constructed robot within the sealed chamber.

Figure 8:
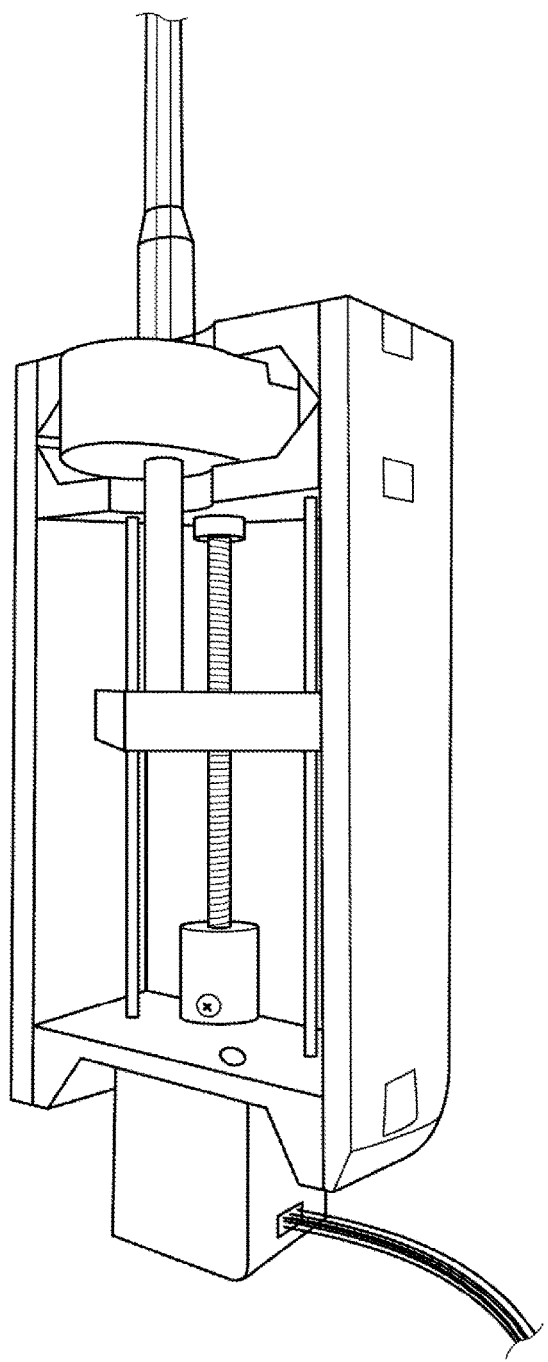
FIG. 8 is an image depicting an manufactured syringe pump.

A syringe pump to deliver solution to the robot was also manufactured using 3-D printing (FIG. 8). The pump allows for easy addition of multiply spinning reservoirs to the system and was tested with up to two concurrent spinners. The pump produced carriage movements as small as 440 nm, or 25 nL droplets from a 3 mL syringe, with a minimum emptying time of 10 seconds. The manufactured syringe pump is inexpensive, and easy to control.

Figure 9:
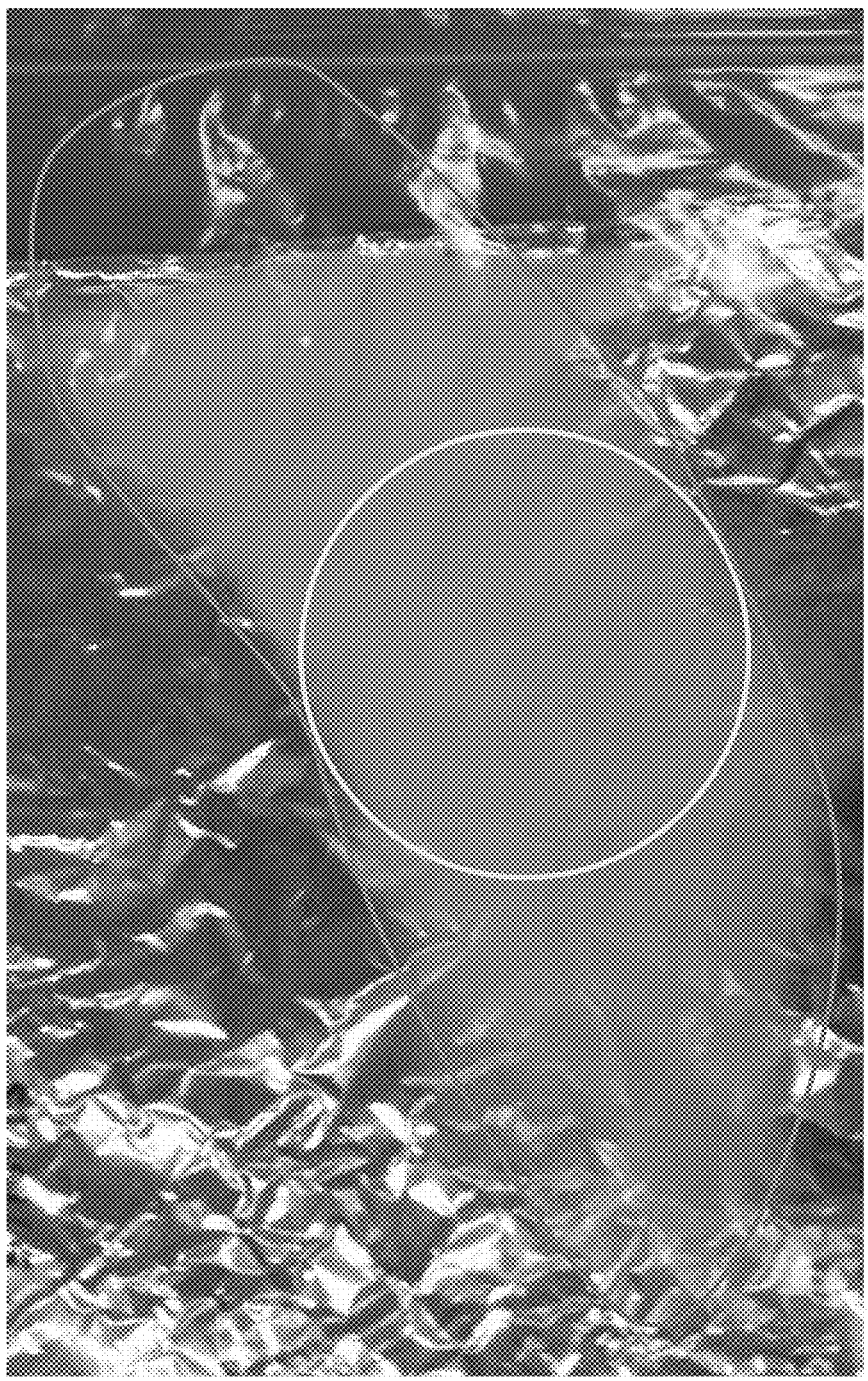
FIG. 9 is an image of a material (outer outline) generated by the system of the invention when the head is programmed to move in an arc. The inner outline refers to a material generated using a traditional setup.

The design presented herein enables free movement in greater than 10 cm×10 cm×15 cm space with a resolution better than 0.01 mm. This has enabled the creation of seamless scaffolds covering an area many times larger than possible in a fixed system. For example, FIG. 9 depicts a polystyrene scaffold spun while the robot moved in an arc (movement depicted in blue), compared to what would be possible in a standard setup (yellow). Additionally the electronic components are well isolated from the system and result in no observable interference.

Figure 10:
FIG. 10 is an image of a "T-shaped" material generated by the system of the invention.

FIG. 10 depicts a "T-shaped" scaffold produced by the present system demonstrating that the robotic system of the invention is capable of producing irregularly shaped objects due to the 3-D motion of the spinneret head.

Example 2: Electric Field Simulations

The effect of the electrodes and components on the generated electrical field and resultant collection of fibers was simulated using MATLAB.

Figure 11:
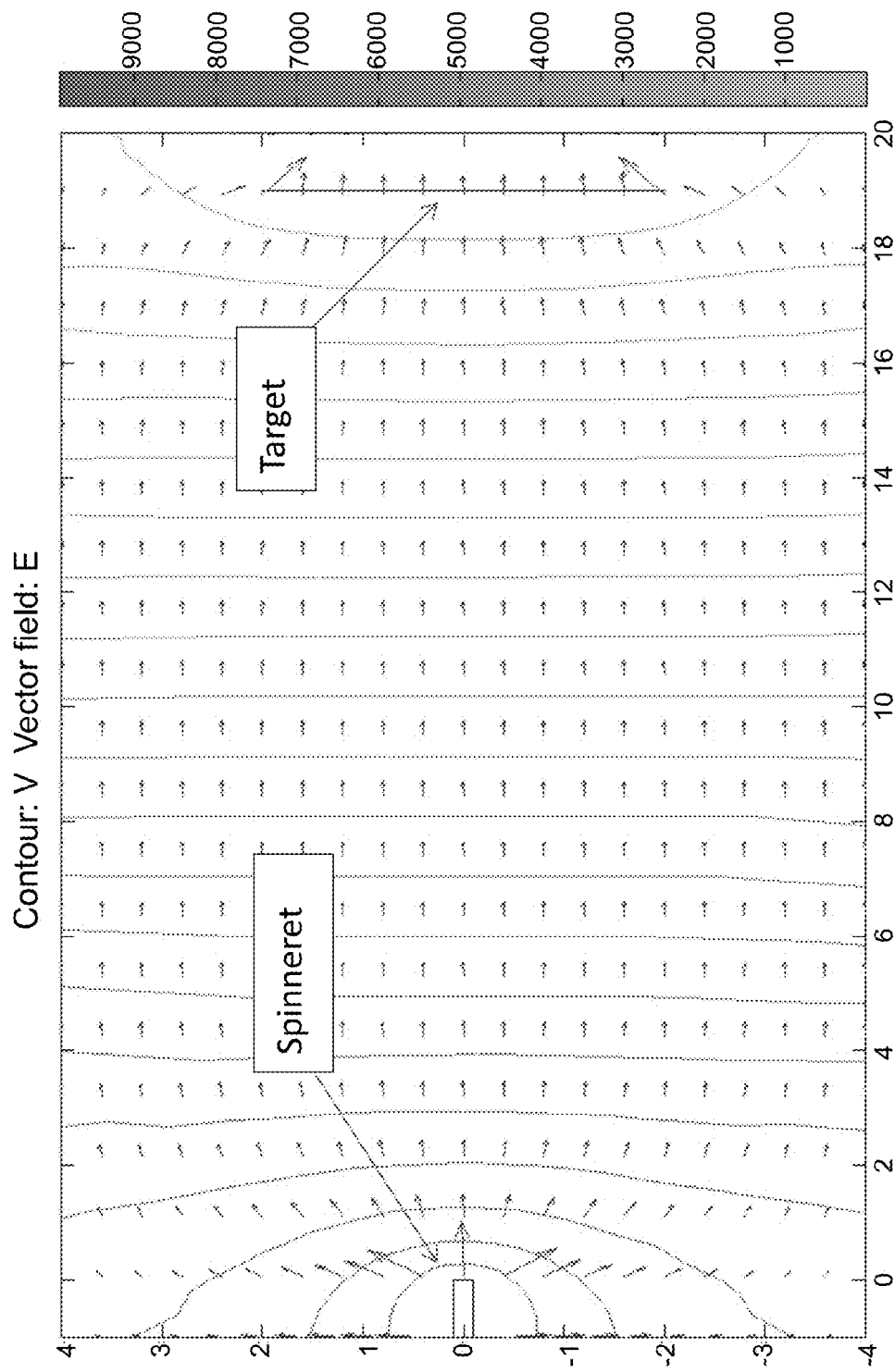
FIG. 11 depicts the electrical field between a spinneret needle and a target.

FIG. 11 shows electrical field lines in a traditional setup. Note that fibers that leave the central axis, have no reason to return, leading to a disperse and uneven mat deposited on the target. In this setup, the target is grounded, a voltage of 10 kV is applied to the spinneret, and the distance from spinneret to target is 19 cm.

Figure 12:
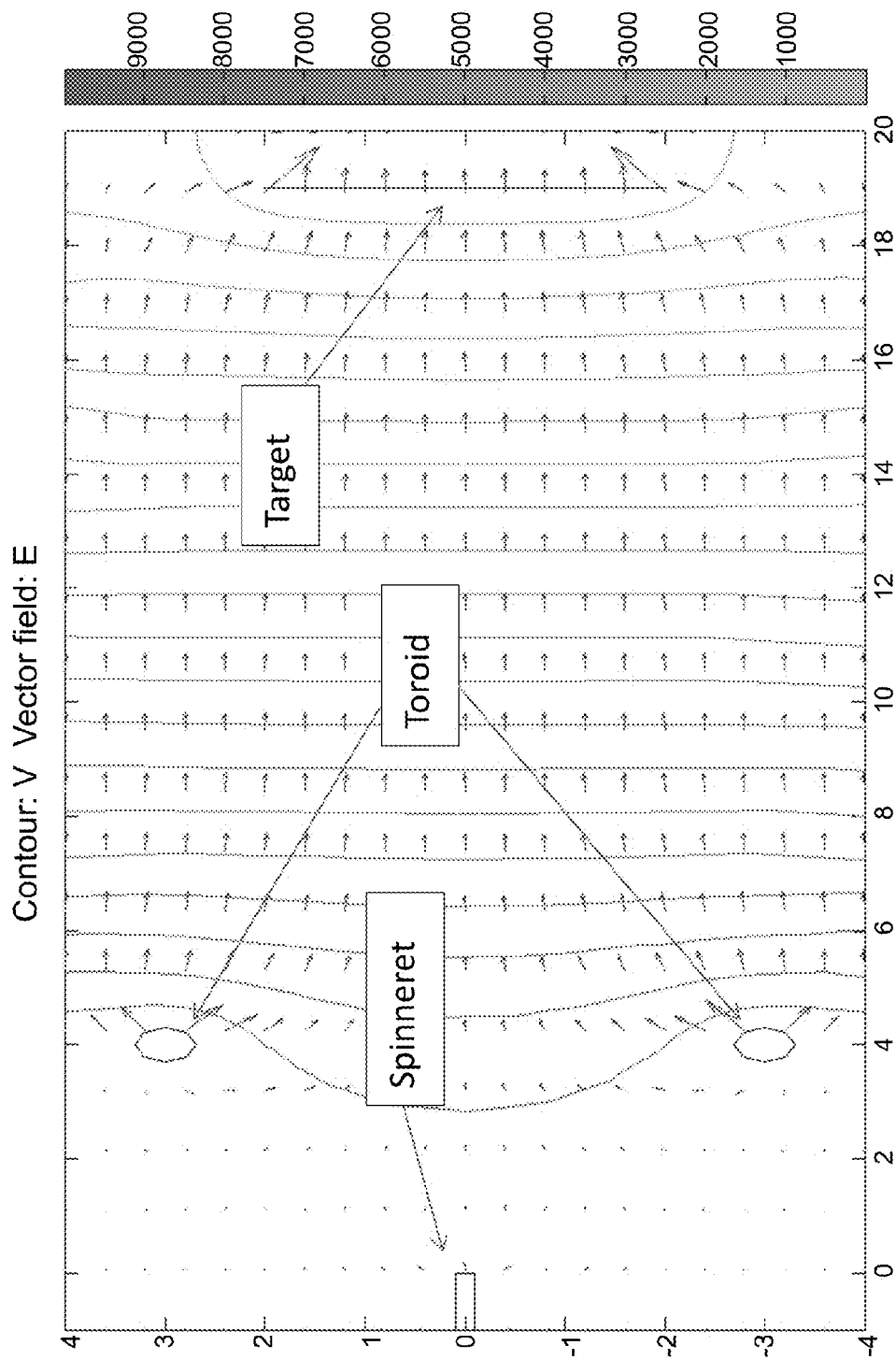
FIG. 12 depicts electrical field lines using a donut shaped toroid auxiliary electrode.

FIG. 12 shows electrical field lines using a donut shaped toroid auxiliary electrode (6 cm diameter, 4 cm from spinneret tip). In this simulation the toroid is charged identically as the spinneret, and the only grounded item is the target positioned to the right. Here, it can be seen that fibers tend to focus in the middle of the target slightly.

Figure 13:
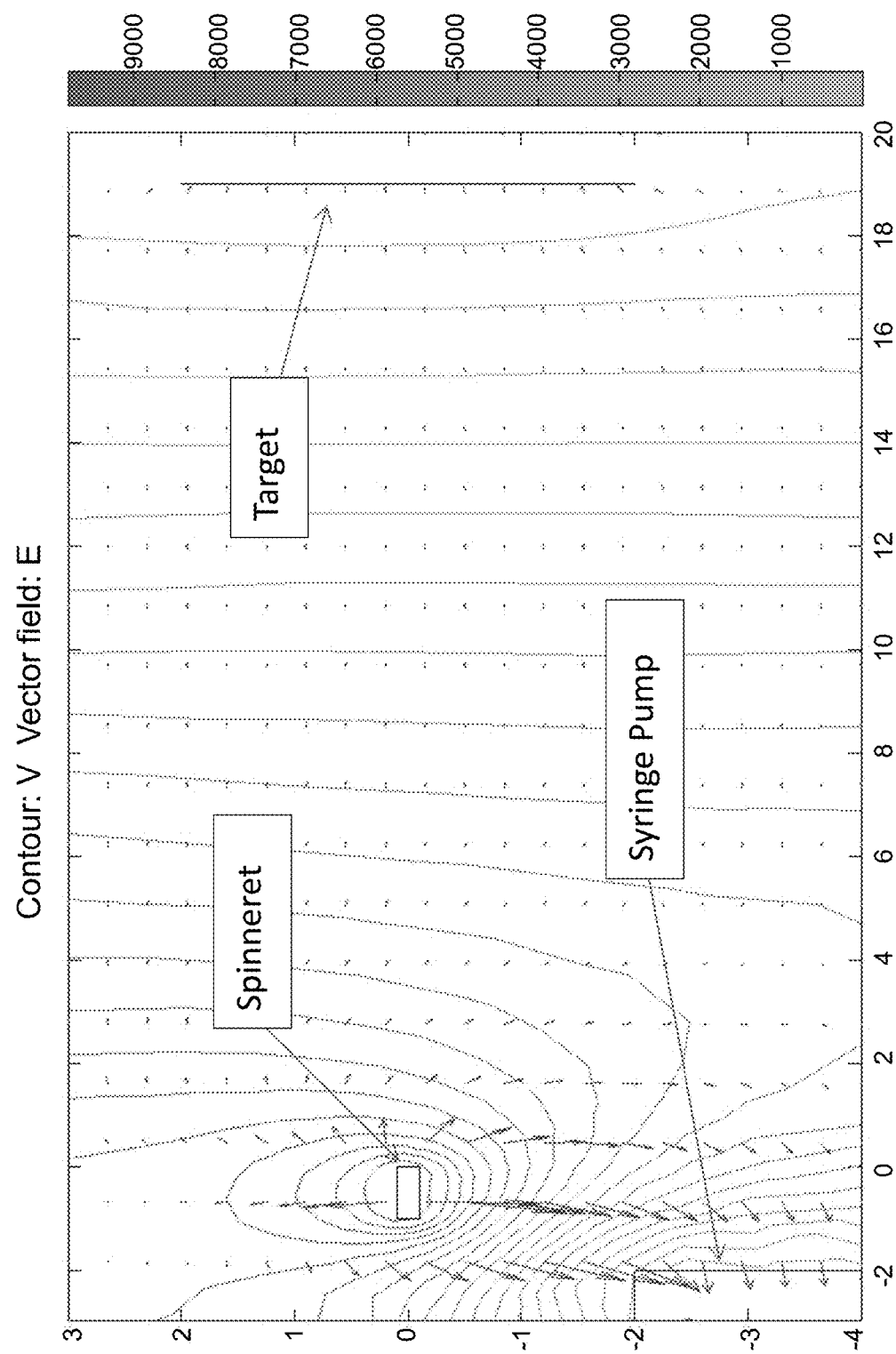
FIG. 13 depicts electrical field lines in a setup having an accessible syringe pump, demonstrating that the presence of the syringe pump alters the generated electric field.

Simulations were performed to examine how additional grounded components within the spinning environment may alter spinning evenness. For example, FIG. 13 shows a setup which includes the syringe pump within the environment. It is observed that the electrical field is altered by the pump, which causes a portion of the electrospun sample to be lost to the surface of the pump. Further, it was observed that fibers tended to accumulate on the bottom of the target.

Figure 14:
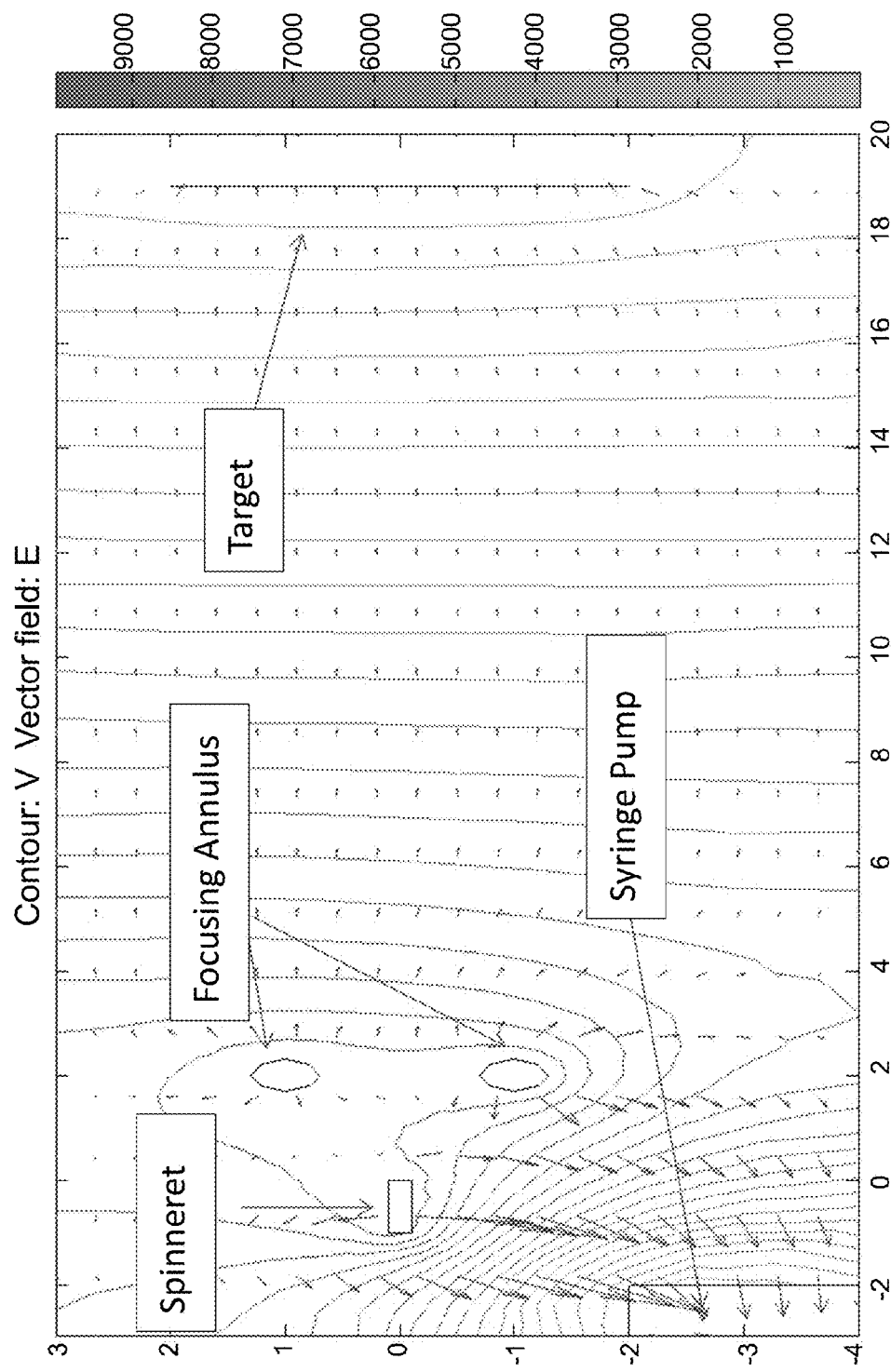
FIG. 14 depicts electrical lines in a setup where a hoop is positioned too close to the spinneret, demonstrating that spinning to the target can be blocked entirely, as the pump becomes the new target.

As shown in FIG. 14, if the hoop is positioned too close to the spinneret, spinning to the target can be blocked entirely, as the pump becomes the new target. These simulations demonstrate the need for an isolated chamber that is free of any interfering components.

Example 3: Electrospinning on a Sloped Surface Target

Figure 15A:
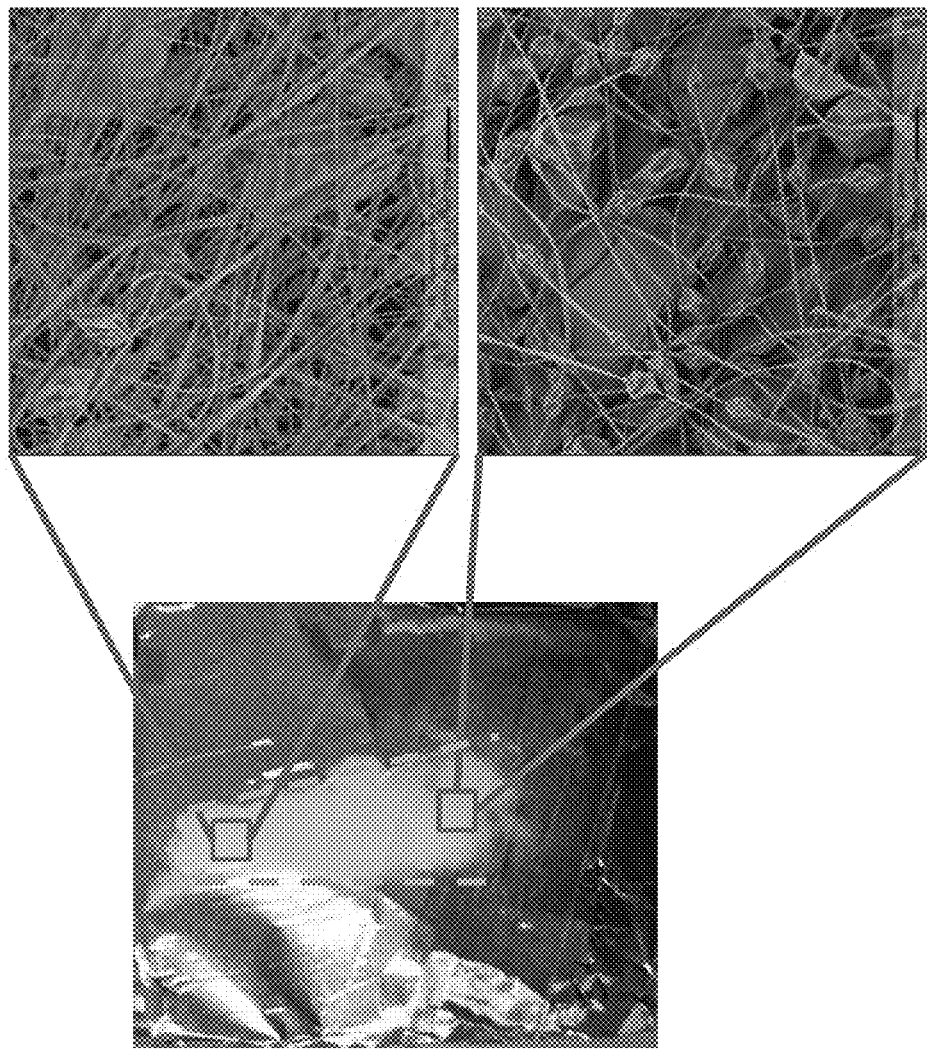
FIG. 15A through FIG. 15C, depicts the results of an experiment of coating a sloped surface by moving the spinneret head in only one axis (FIG. 15A) and by moving the spinneret head in two directions (FIG. 15B). It is observed that moving the head along the X and Z axes to provide a constant separation distance from the sloped surface to the head resulted in superior control over the resultant spun coating and more consistent fiber geometry, as measured by mean fiber diameter (FIG. 15C).
Figure 15A:
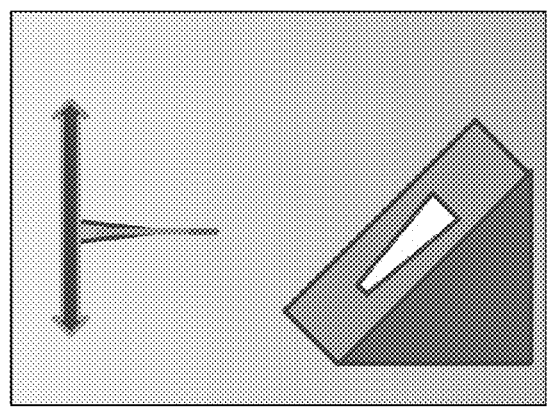
Figure 15B:
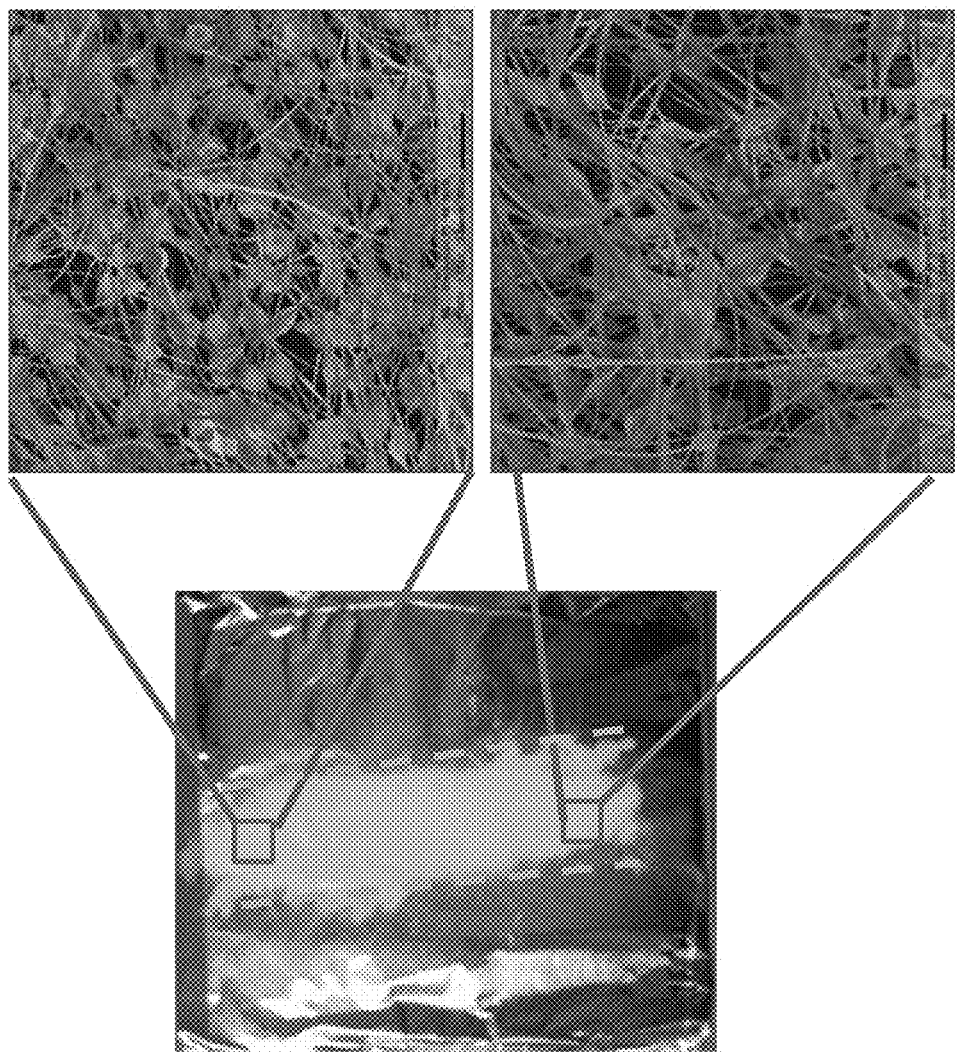
Figure 15B:
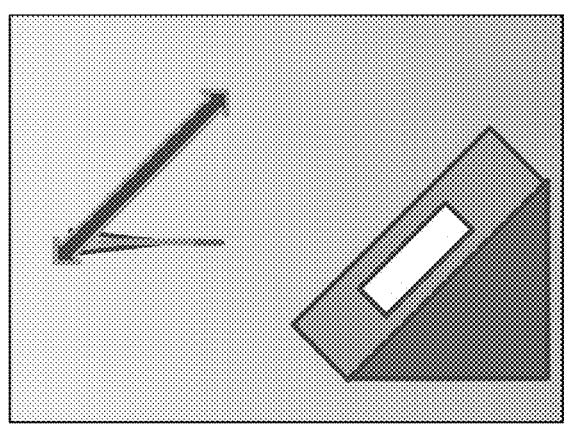
Figure 15C:
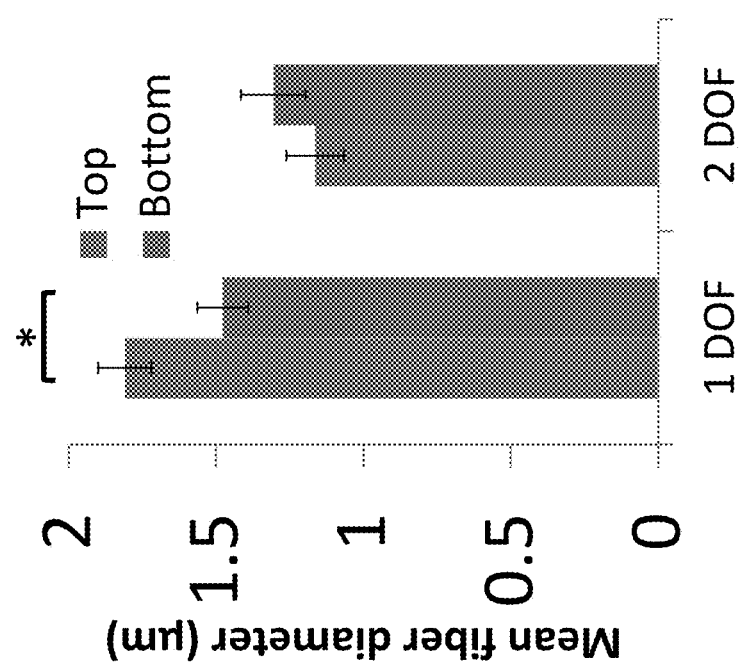

Experiments were performed to compare the resultant electrospun mat produced via limiting robot motions to the X axis and produced via allowing robot motion in the X and Z axes to follow a sloped target geometry. Electrospinning of polystyrene was performed using the two different methodologies, onto a rectangular prism having a sloped surface (a four inch rise over a four inch run). When robot motion is restricted to motion in the X axis, it is observed that there was low coverage at the more 'distant' areas and gradual widening of the spun area (FIG. 15A). The two SEM images obtained from the two ends of the electrospun mat show that fiber diameter and thickness are also highly variable. However, when the robot is allowed to move in the X and Z axes and is programmed to follow the target geometry, maintaining a constant spinning distance, it was observed that the resultant mat exhibited enhanced coverage and more even fiber distribution (FIG. 15B). This effect is quantified by measuring the mean fiber diameter at the top and bottom of the electrospun mats in both conditions. It is seen that the mean fiber diameter is significantly different when motion is restricted to only the X-axis (1 DOF), whereas mean fiber diameter is not different when motion was allowed in the X and Z axes (2 DOF) (FIG. 15C).

Example 4: Electrospinning on a Biologically Relevant Irregular Surface

Experiments were conducted to use the devised system for electrospinning on a complex, 3-D, and biologically relevant, substrate. The distance from the spinneret to a collector or target is an important variable in electrospinning. So long as scaffolds are always flat (or cylindrical) fibers may be fairly evenly deposited. Unfortunately, using standard electroprocessing systems, if it is desired to coat biological surfaces which are not uniform, it is difficult to produce uniform fibers.

Using an exemplary system of the invention, comparison studies were done by applying a thin scaffold onto a hip bone when tracking the contour of the bone (i.e., robot was moved to maintain a constant distance between the surface and spinneret) and in a non-tracking procedure, where the separation distance changes based upon the uneven contour of the bone. The scaffold were spun onto the lower half a hip bone, a surface shape not typically conducive to electrospinning due to its bowed nature. Specifically, even when oriented to be as flat as possible, the shape resembles a 165 mm long crescent, with edges rising 75 mm from the central lowest point. Considering that electrospinning often leverages spinning distances close to this distance, such a significant change in height can result in extremely uneven spinning behavior. Furthermore, the item in question takes a majority of the spinning chamber, which is not an issue with the robot design indicated as the outer surface is an insulator, but in a metal robot, such an attempt would cause arcing and extremely unpredictable spinning.

For tracking based spinning, a map of the surface contour was programmed into the robot described, and a polystyrene scaffold was spun following the contour 120 mm from the surface. The spun solution was 20% polystyrene (Styron 610) dissolved in tetrahydrofuran (Alfa Aesar 22904), which was pumped at 5 µl/min. The voltage was set to 28 KV (Gamma high voltage). An electrified ring is placed around the spinneret to help focus the deposited fibers. The resulting scaffold not only covered the entire surface, but even fiber morphology was observed between both the 'close' and 'far' portions.

To emulate the common 2-dimensional control methods (non-tracking), the robot was programmed to follow the same contour with a fixed distance of 120 mm from the highest point, a control from the lowest point wasn't possible due to the strength of the electric field at the ends of the crescent. This means the 'deep' central area was about 195 mm away. The non-tracking methods is meant to mimic a robot capable only of movement in the X and Y axis The spun solution was 20% polystyrene (Styron 610) dissolved in tetrahydrofuran (Alfa Aesar 22904), which was pumped at 5 µl/min. The voltage was set to 28 KV (Gamma high voltage).

Figure 16:
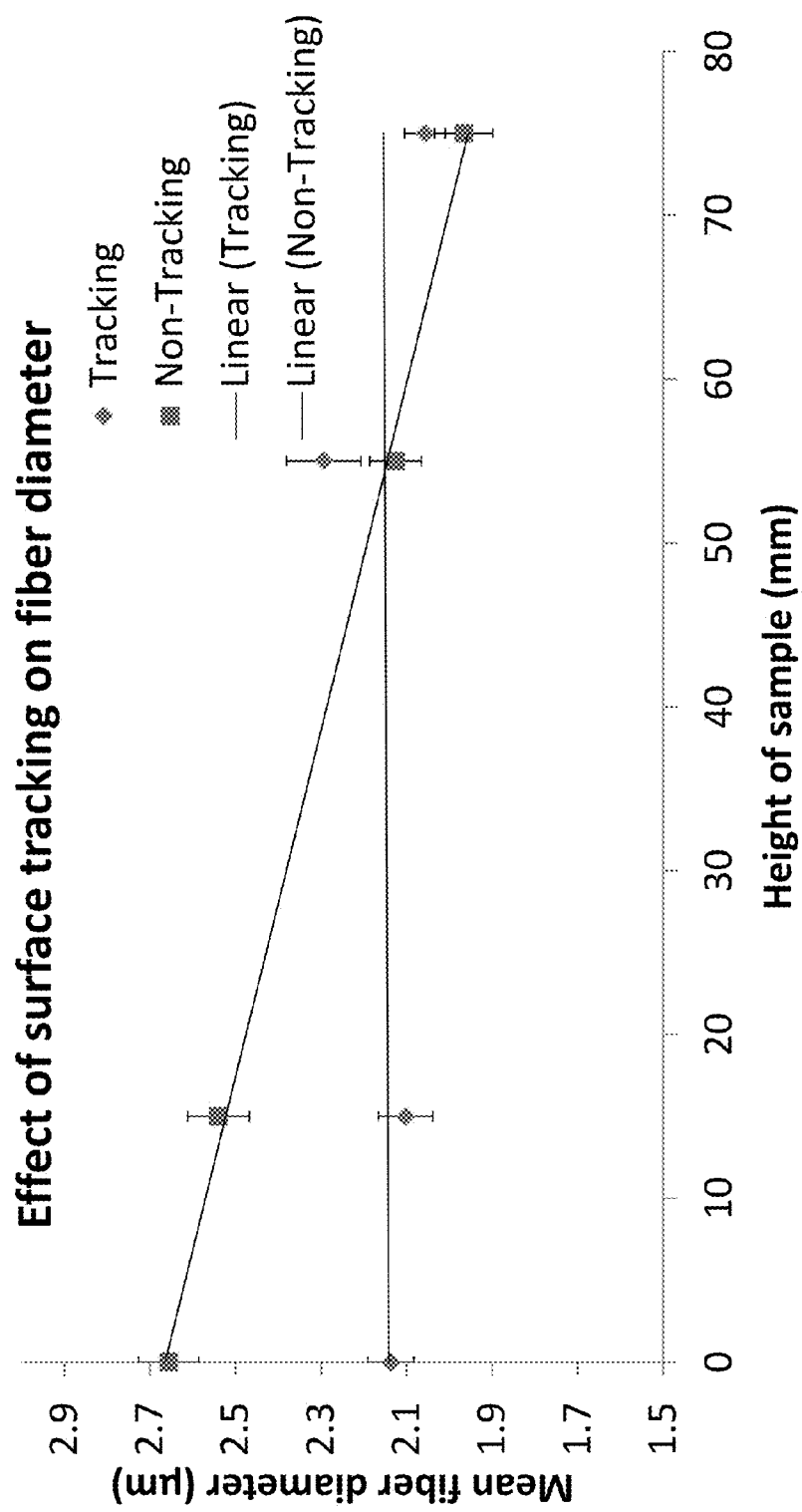
FIG. 16 depicts the results of an experiment of coating an irregular shaped hip bone by moving the spinneret head along the X and Y axis (non-tracking) versus moving the spinneret head along the X, Y, and Z axis to provide a constant separation distance between the surface and head (tracking). It was observed that tracking, by allowing movement of the head in all three directions, produced a spun coating with more consistent fiber geometry.

To quantify the differences between the tracking method and non-tracking method, the fiber diameter produced by the two methods was quantified. Samples were cut from 4 places on the bone and imaged by 485 nm reflected light on an Olympus laser scanning confocal microscope. For each region, 15 fibers were measured in 3 frames. It was observed that the mean fiber diameter remained substantially constant using the tracking method made possible the robot motion of the system, while mean diameter decreased as the height of sample increased when using the traditional non-tracking method (FIG. 16). The height of sample is the distance along the Z-axis from the lowest point on the bone surface. Thus, in the non-tracking case, a height of 0 mm would correspond to a spinning distance of 195 mm, and a height of 75 mm a spinning distance of 120 mm.

It was thus observed that the farther from the spinneret, the larger the fibers became. At the closest, the fibers from the non-tracking setup matched the tracking setup, as the distance matched here. For regions that were further from this distance, more variation was seen. To maintain good coverage, and fiber homogeneity, it is important to use all 3 degrees of freedom while spinning Furthermore, it should be noted that the hip bone is roughly 20 cm across, and the box is only 30 cm wide. To be able to fit an item so near to the size of the box is impossible in metal designs, as the spinneret will short and arc to the wall, especially if using a focus ring. Further, the ability to produce uniform fiber diameters by providing a constant separation distance also means that scaffolds can be made having regions of differing fiber morphologies, if desired, by purposely altering separation distance using the robot of the system.

Example 5: Electrospinning of Multiple Fibers

The head was attached to two automated syringe pumps. The pumps are controlled from the same microcontroller, so the robot and pumping speed can be controlled by a single interface. Voltage has been controlled by the same interface as well. One pump contained 20% polystyrene in THF solution, while the second pump contained 20% polystyrene in THF that was first saturated with Riboflavin (vitamin B2). Thus, the two solutions were identical except for the loaded Riboflavin. Two spinnerets are side by side on the head, and the solutions are pumped one at a time, allowing for control over which fiber type is deposited.

A scaffold was spun 9 cm long and 4 cm wide from polystyrene. Two spots were then spun on either end that included the riboflavin containing fibers. The center 60 mm×24 mm section was cut out to facilitate imaging.

Figure 17:
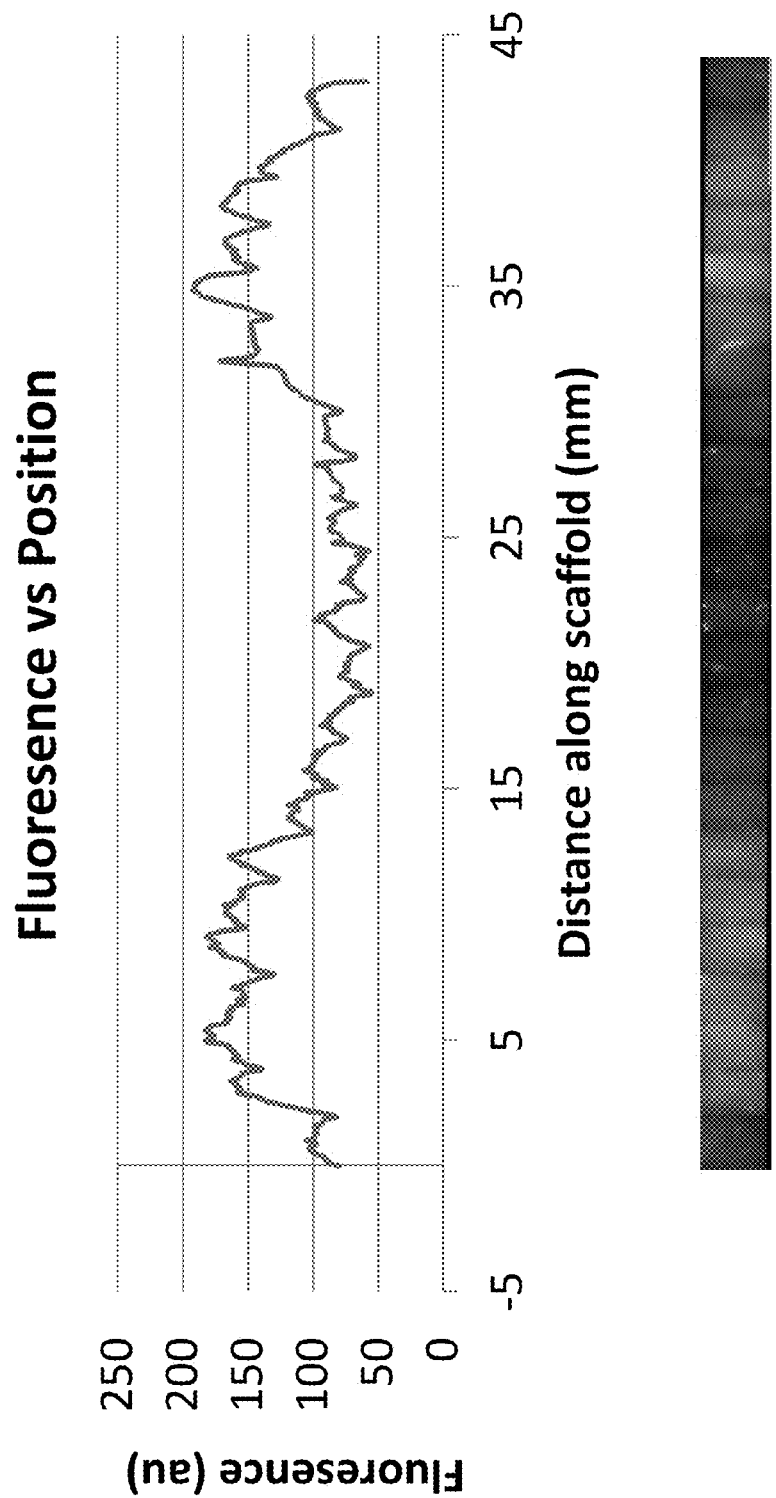
FIG. 17 depicts the results of an experiment of electrospinning of two different types of fibers from two different spinnerets. The system was used to deposit riboflavin containing fibers specifically at the two ends of the spun scaffold. The graph and image, illustrating the fluorescence of the deposited riboflavin, demonstrate that the resultant mat had riboflavin positioned at the two ends.

Riboflavin is fluorescent and the green fluorescence is used to quantify amount embedded using an Olympus FSX 200 to stich a 4× image across the middle. As can be seen by the image and graph of FIG. 17, the robot was able to specifically position riboflavin containing fibers at the two ends of the scaffold. Thus the system may be used for precise organization of loaded fibers across the scaffold. Additional spinnerets or other printing or extruding methods build upon this design to produce even more complex scaffold designs. Using high precision deposition methods, intricate designs can be drawn in all three dimensions, including, for example the extruding of growth factor above or below any layer of interest.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A robotic electroprocessing system, comprising:
   a spinneret head;
   at least three linear actuators connected to the spinneret head;
   a target; and
   a motor that drives movement of the linear actuators;
   wherein the target, the spinneret head and the at least three linear actuators are positioned in an environmentally sealed chamber.

2. The system of claim 1, wherein each of the at least three actuators are connected to a first end of one or more arms, wherein the second end of the one or more arms are connected to the spinneret head.

3. The system of claim 2, wherein the arms are connected to the actuators and spinneret head using universal joints providing at least two degrees of freedom.

4. The system of claim 1, wherein the spinneret head comprises one or more needles capable of being electrified.

5. The system of claim 4, wherein the one or more needles are connected via tubing to one or more fluidic pumps located exterior to the chamber.

6. The system of claim 1, wherein the chamber provides a controlled isolated environment.

7. The system of claim 1, wherein the chamber further comprises one or more auxiliary electrodes.

8. The system of claim 1, wherein each of the at least three actuators comprises a movable carriage connected to the spinneret head, wherein the carriage moves along the actuator as driven by the motor, thereby moving the spinneret head.

9. The system of claim 8, wherein the motor is a stepper motor which turns a screw of the actuator, thereby moving the carriage.

10. The system of claim 4, wherein the chamber is devoid of conductive materials which would interfere with an electrical field generated by voltage supplied to the one or more needles of the spinneret head.

11. The system of claim 1, wherein the spinneret head moves in three dimensions in order to provide a constant distance along the Z-axis, between the spinneret head and the target, while moving along the X or Y axis, thereby allowing for electroprocessing onto targets with surfaces of irregular heights for the production of irregular shaped material.

12. The system of claim 1, wherein the spinneret head moves at a resolution of less than about 10 μm.

13. The system of claim 1, wherein the target rotates.

14. The system of claim 13, wherein the rotation of the target allows for coating of irregular shaped 3-D materials.

15. The system of claim 1, wherein the system further comprises a computing device which controls the movement of the spinneret head and environment within the chamber.

16. A method of manufacturing a material comprising the steps of:
   providing the robotic electroprocessing system of claim 1 comprising a spinneret head, at least three linear actuators connected to the spinneret head, a target, and a motor that drives movement of the linear actuators;
   administering a fluid comprising at least one component to be deposited to at least one needle positioned on the spinneret head; and
   producing an electrical field between the at least one needle and the target, thereby depositing the component onto the target.

17. The method of claim 16, wherein the method comprises moving the spinneret head in three-dimensions to deposit the component at a desired location of the target.

18. The method of claim 16, comprising depositing the component onto a surface having irregular heights by moving the spinneret head to provide a constant distance along the Z-axis between the spinneret head and the target, while moving along the X or Y axis.

19. The method of claim 18, wherein the method produces irregular shaped materials.

20. The method of claim 16, wherein the method manufactures a material that is biocompatible.

21. The method of claim 16, wherein the component is chosen from a group consisting of a natural component, synthetic component, and a biological component.

22. The method of claim 16, wherein the generated electrical field and component deposition is not interfered with by the presence of conductive materials within the chamber.

23. The method of claim 16, wherein the method manufactures a material that is a scaffold for tissue engineering.

24. The method of claim 16, wherein the method comprises electroprocessing of at least one component and printing of at least one component.

25. The method of claim 16, wherein the method comprises electrospinning of at least one component and electrospraying of at least one component.

26. The method of claim 16, further comprising rotating the target, thereby depositing the component onto a rotating target.

27. The method of claim 26, wherein the method coats irregular shaped 3-D materials.

* * * * *